United States Patent
Kowari et al.

(10) Patent No.: US 8,840,851 B2
(45) Date of Patent: Sep. 23, 2014

(54) PIPETTE TIP SUPPLYING APPARATUS, SAMPLE ANALYZER AND PIPETTE TIP SUPPLYING METHOD

(75) Inventors: Takeo Kowari, Kobe (JP); Makoto Ueda, Hyogo (JP)

(73) Assignee: Sysmex Corporation, Kobe (JP)

( * ) Notice: Subject to any disclaimer, the term of this patent is extended or adjusted under 35 U.S.C. 154(b) by 251 days.

(21) Appl. No.: 13/355,752

(22) Filed: Jan. 23, 2012

(65) Prior Publication Data

US 2012/0195798 A1    Aug. 2, 2012

(30) Foreign Application Priority Data

Jan. 27, 2011    (JP) .................................. 2011-015138

(51) Int. Cl.
*B01L 3/02*       (2006.01)
*B01L 9/00*       (2006.01)
*G01N 35/10*      (2006.01)
*G01N 35/04*      (2006.01)

(52) U.S. Cl.
CPC .......... *G01N 35/04* (2013.01); *G01N 2035/103* (2013.01); *G01N 2035/0491* (2013.01); *G01N 2035/0427* (2013.01)
USPC ............. 422/511; 422/526; 422/564; 422/65; 422/67; 221/9; 221/10

(58) Field of Classification Search
CPC .... B01L 9/543; B65G 47/14; B65G 47/1414; B65G 47/24; B65G 47/256
USPC ............. 422/526, 564, 525, 552, 63–65, 511, 422/67; 206/557–563; 211/126.1, 126.7; 221/9–10
See application file for complete search history.

(56) References Cited

U.S. PATENT DOCUMENTS

| | | | |
|---|---|---|---|
| 488,084 A * | 12/1892 | Miner ........................... | 221/238 |
| 7,299,943 B2 * | 11/2007 | Itoh ........................... | 221/312 R |
| 2004/0108330 A1 | 6/2004 | Itoh | |
| 2007/0148042 A1 | 6/2007 | Ootani et al. | |
| 2009/0078717 A1 * | 3/2009 | Kowari et al. ..................... | 221/1 |

* cited by examiner

*Primary Examiner* — Brian R Gordon
(74) *Attorney, Agent, or Firm* — Brinks Gilson & Lione

(57) ABSTRACT

The present invention is a pipette tip supplying apparatus which comprises: a storing section configured to store a plurality of pipette tips; a supplying section configured to supply at least one of the plurality of pipette tips stored in the storing section outside the storing section; a detector configured to detect a pipette tip assembly in which one pipette tip and another pipette tip are piled up with a distal end of the one pipette tip inserted into the another pipette tip; and a discharging section configured to discharge the pipette tip assembly from the storing section, when the detector has detected the pipette tip assembly in the storing section.

14 Claims, 17 Drawing Sheets

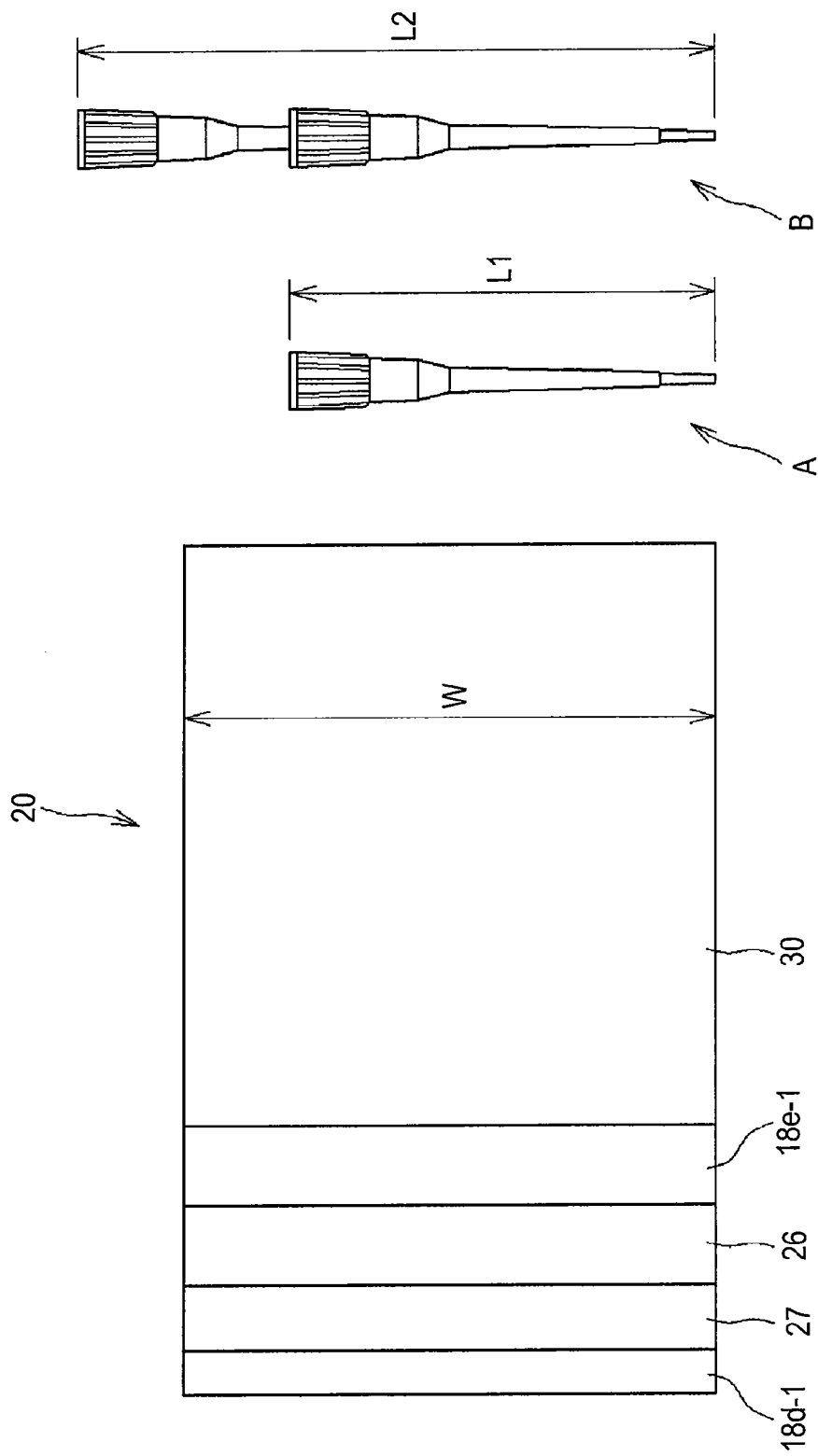

PIPETTE TIP SUPPLYING APPARATUS, SAMPLE ANALYZER AND PIPETTE TIP SUPPLYING METHOD

RELATED APPLICATIONS

This application claims priority under 35 U.S.C. §119 to Japanese Patent Application No. 2011-015138 filed on Jan. 27, 2011, the entire content of which is hereby incorporated by reference.

BACKGROUND OF THE INVENTION

1. Field of the Invention

The present invention relates to a pipette tip supplying apparatus, a sample analyzer, and a pipette tip supplying method.

2. Description of the Related Art

Conventionally, a pipette tip has been used in dispensing of a sample such as blood and urine, and a pipette tip supplying apparatus which automatically supplies the pipette tip to a position at which the pipette tip is mounted on a sample analyzer has been known.

For example, U.S. Patent Publication No. 2004/108330 discloses an automatic dispensing tip supplying apparatus which includes a storage box into which a plurality of pipette tips are supplied by a user, a feeding mechanism which lifts pipette tips, collected at a bottom of the storage box, one by one, and a conveyor which transports a pipette tip that is carried out to the outside of the storage box by the feeding mechanism.

In some cases, in the storage box, there is a pipette tip assembly in which one pipette tip and another pipette tip are piled up with a distal end of the one pipette tip inserted into the another pipette tip. The feeding mechanism has a lifting plate which is driven in the vertical direction and on which only one pipette tip can be laid. The U.S. Patent Publication No. 2004/108330 has a description that, among pipette tips lifted by the lifting plate of the feeding mechanism, the pipette tip assembly drops again to the bottom of the storage box when the lifting plate is moved downward.

However, even in the dispensing tip supplying apparatus disclosed in the U.S. Patent Publication No. 2004/108330, it is difficult to completely prevent the pipette tip assembly from being carried out to a side of the pipette tip mounting position by the lifting plate.

SUMMARY OF THE INVENTION

The scope of the present invention is defined solely by the appended claims, and is not affected to any degree by the statements within this summary.

A first aspect of the present invention is a pipette tip supplying apparatus comprising: a storing section configured to store a plurality of pipette tips; a supplying section configured to supply at least one of the plurality of pipette tips stored in the storing section outside the storing section; a detector configured to detect a pipette tip assembly in which one pipette tip and another pipette tip are piled up with a distal end of the one pipette tip inserted into the another pipette tip; and a discharging section configured to discharge the pipette tip assembly from the storing section, when the detector has detected the pipette tip assembly in the storing section.

A second aspect of the present invention is a sample analyzer comprising: a sample dispenser that comprises an aspiration nozzle on which a pipette tip is mounted and that is configured to dispense a sample with the pipette tip mounted on the aspiration nozzle; an analysis section configured to analyze the sample dispensed by the sample dispenser; a storing section configured to store a plurality of pipette tips; a supplying section configured to supply at least one of the plurality of pipette tips stored in the storing section to a position at which a pipette tip is mounted on the aspiration nozzle; a detector configured to detect a pipette tip assembly in which one pipette tip and another pipette tip are piled up with a distal end of the one pipette tip inserted into the another pipette tip; and a discharging section configured to discharge the pipette tip assembly outside the tip storing section, when the detector has detected the pipette tip assembly in the storing section.

A third aspect of the present invention is a pipette tip supplying method, comprising steps of: (a) performing an operation for detecting a pipette tip assembly in a storing section capable of storing a plurality of pipette tips, wherein the pipette tip assembly includes one pipette tip and another pipette tip which are piled up with a distal end of the one pipette tip inserted into the another pipette tip; (b) discharging the pipette tip assembly from the storing section when the pipette tip assembly has been detected by the step (a); and (c) supplying at least one of the plurality of pipette tips stored in the storing section to a position at which a pipette tip is mounted on a sample aspiration nozzle.

BRIEF DESCRIPTION OF THE DRAWINGS

FIG. 17 is a diagram for comparing the width of the pipette tip storing section to the length of a pipette tip.

DETAILED DESCRIPTION OF THE PREFERRED EMBODIMENTS

Hereinafter, embodiments of the invention will be described on the basis of the drawings.

(1. Entire Configuration of Sample Analyzer)

Figure 1:
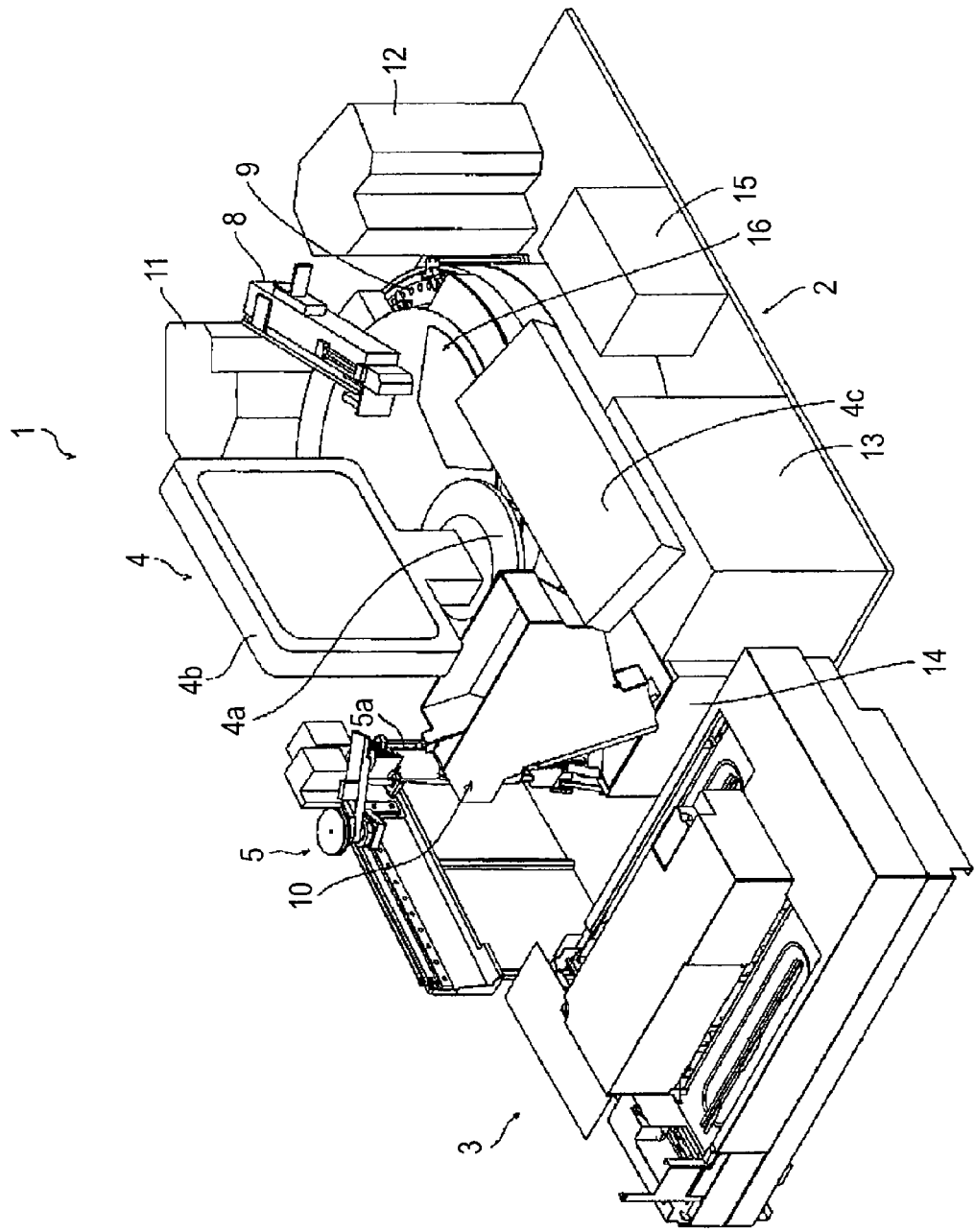
FIG. 1 is a perspective view showing the entire configuration of a sample analyzer of the invention.
Figure 2:
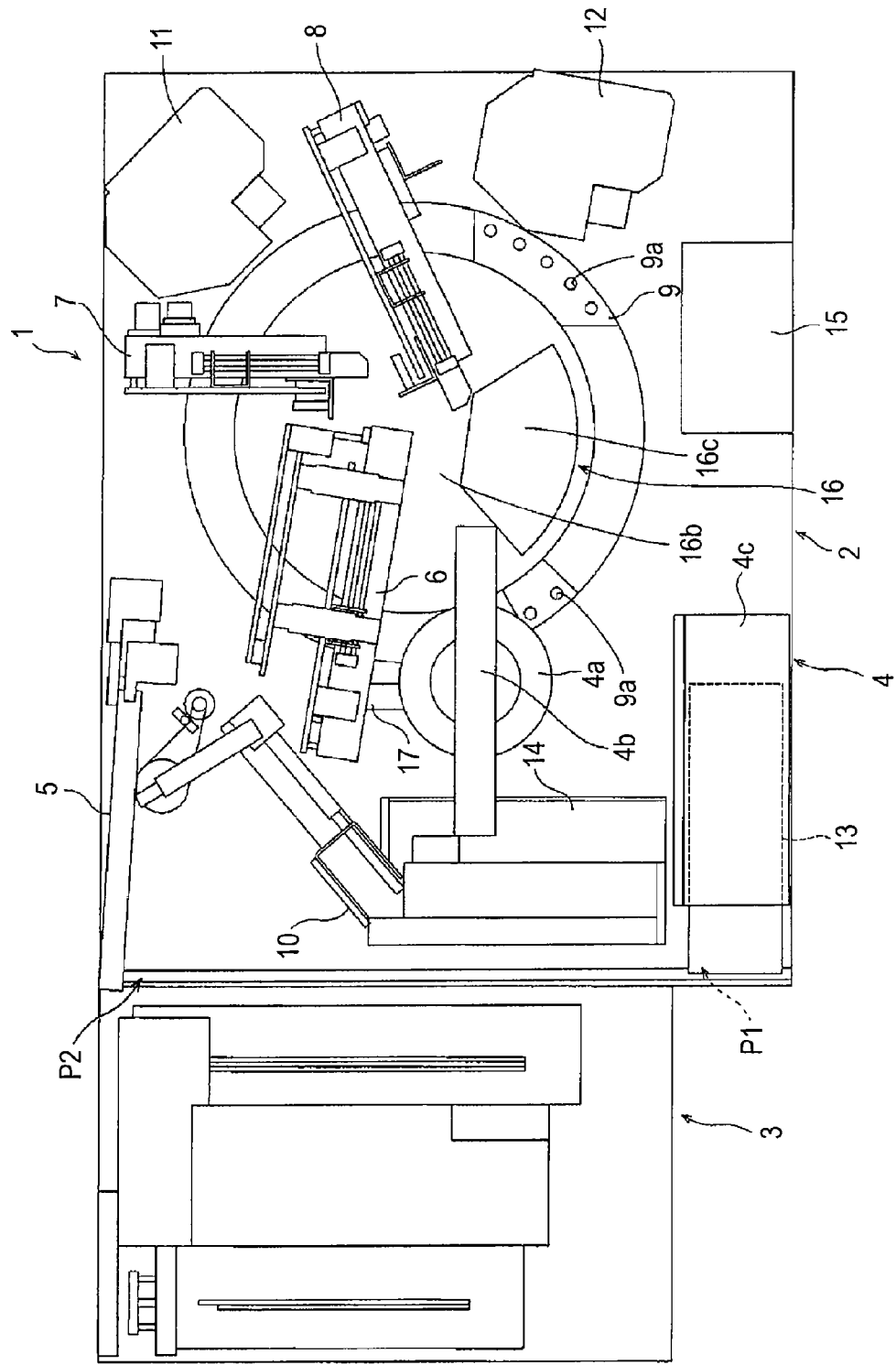
FIG. 2 is a plan view of the sample analyzer.

A sample analyzer 1 of the invention is, for example, an apparatus which performs quantitative or qualitative measurement of antigens, antibodies and the like included in a sample such as blood which is a measurement target. As shown in FIGS. 1 and 2, the sample analyzer 1 is provided with a measurement mechanism section 2, a sample transport section 3 which is disposed adjacent to the measurement mechanism section 2, and a controller 4 which is electrically connected to the measurement mechanism section 2.

Figure 16:
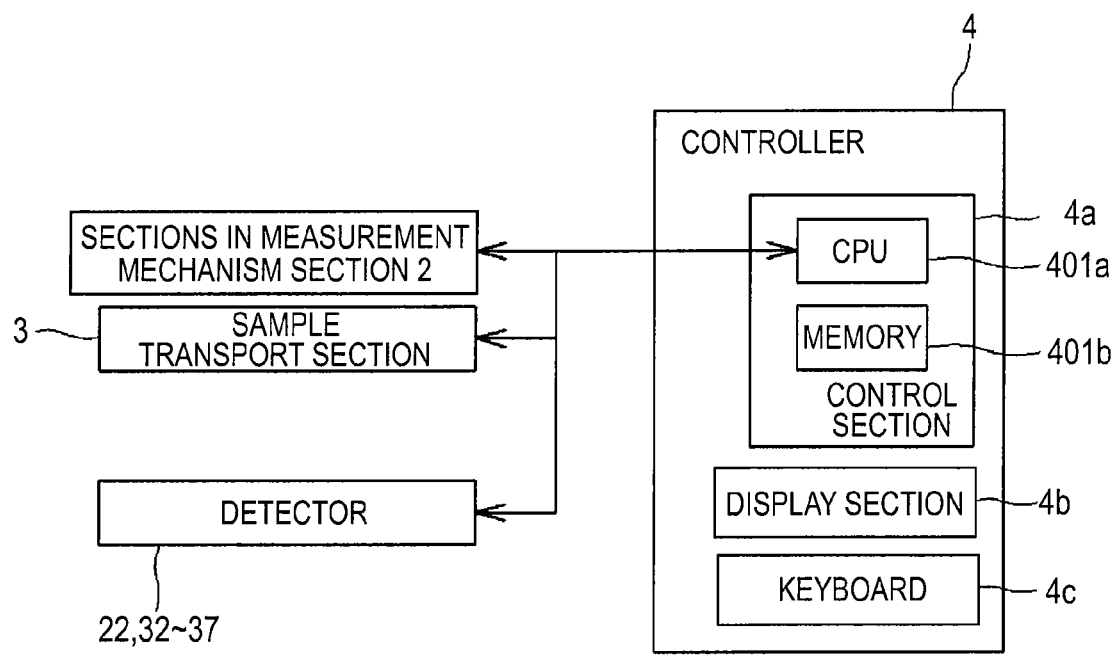
FIG. 16 is a block diagram showing the configuration of a controller.

The sample transport section 3 can transport a rack which holds a plurality of test tubes (not shown) containing a sample, and transports a test tube containing a sample to a position at which the sample is aspirated by a sample dispensing arm 5. The controller 4 is formed of a personal computer, and has a control section 4a, a display section (monitor) 4b, and a keyboard 4c. The control section 4a includes a CPU 401a, a memory section 401b and the like as shown in FIG. 16, and has a function of transmitting an operation start signal to the respective sections of the measurement mechanism section 2 and the sample transport section 3 and analyzing the sample information obtained by the measurement mechanism section 2. The memory section 401b is formed of a ROM, a RAM, a hard disk and the like, and stores computer programs, data and the like which are used in the process by the CPU 401a. In addition, the CPU 401a receives a detection signal from each of detectors 22 and 32 to 37 to be described later. In addition, the display section 4b can display various kinds of information and displays analysis results obtained by the control section 4a, notification information for a user, and the like.

The measurement mechanism section 2 is provided with the sample dispensing arm (dispensing section) 5, a pipette tip supplying apparatus 13, and an analysis section 14. In addition, the measurement mechanism section 2 of this embodiment is provided with an R1 reagent dispensing arm 6, an R2 reagent dispensing arm 7, an R3 reagent dispensing arm 8, a reaction section 9, a cuvette supplying section 10, a primary BF separator 11, a secondary BF separator 12, an R4/R5 reagent supplying section 15, and a reagent installation section 16.

The pipette tip supplying apparatus 13 has a function of supplying a plurality of pipette tips A input by a user one by one to a first position P1 for mounting a tip. The first position P1 is a preparation position for mounting a tip on the sample dispensing arm 5 (aspiration nozzle 5a). Furthermore, a transport supply section 40 (see FIG. 4) of the pipette tip supplying apparatus 13 transports a pipette tip A supplied to the first position P1 to a second position P2 for mounting a tip. The second position P2 is an actual tip mounting position on the sample dispensing arm 5 (aspiration nozzle 5a).

A holder 41 (see FIG. 4) which receives a dropped pipette tip A is put on hold at the first position P1, and the transport supply section moves the holder 41 to the second position P2 and transports the pipette tip A to the second position P2.

The sample dispensing arm 5 has the aspiration nozzle 5a on which a pipette tip A (see FIG. 3) having an opening at one end is mounted. At the second position P2 for mounting a tip, the pipette tip A is attached to a distal end of the aspiration nozzle 5a of the sample dispensing arm 5. The sample dispensing arm 5 dispenses a sample in a state in which the pipette tip A is mounted on the aspiration nozzle 5a. That is, after a pipette tip is mounted at the second position for mounting a tip, the sample dispensing arm 5 aspirates a sample in a test tube which is transported to the sample aspiration position by the sample transport section 3, and dispenses (ejects) the sample to a cuvette, positioned at a sample ejection position, to which a reagent R1 (capture antibody) has been dispensed by the R1 reagent dispensing arm 6. Thereafter, the R2 reagent dispensing arm 7 dispenses a reagent R2 (magnetic particles) to the cuvette to bind the magnetic particles to the capture antibody which is bound to the antigen included in the sample in the cuvette. The complex of the bound antigen, capture antibody, and magnetic particles is collected by the magnetism of the primary BF separator 11, and the reagent R1 including the free capture antibody is removed from the cuvette. Next, the R3 reagent dispensing arm 8 dispenses a third reagent (labeled antibody) to the cuvette to bind the labeled antibody to the antigen in the cuvette. The complex of the bound magnetic particles, antigen, and labeled antibody is collected by the magnetism of the secondary BF separator 12, and the third reagent including the free labeled antibody is removed from the cuvette. A reagent R4 (dispersion liquid) and a fifth reagent (luminescent substrate) are further dispensed into the cuvette, and then the cuvette is transferred to the analysis section 14.

The analysis section 14 has a function of analyzing a sample which is dispensed by the sample dispensing arm 5. In this embodiment, the light which is generated in the course of reaction of the luminescent substrate with the labeled antibody which is bound to the antigen of the sample subjected to a predetermined treatment is acquired by a photo multiplier tube, and thus the amount of the antigen included in the sample is measured.

(2. Pipette Tip A)

Figure 3A:
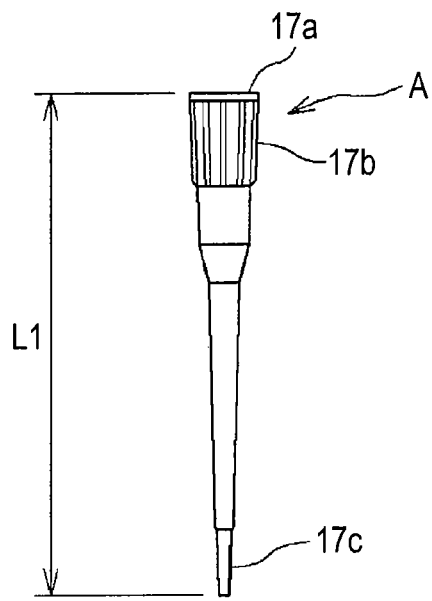
FIG. 3A is a diagram illustrating a pipette tip.
Figure 3B:
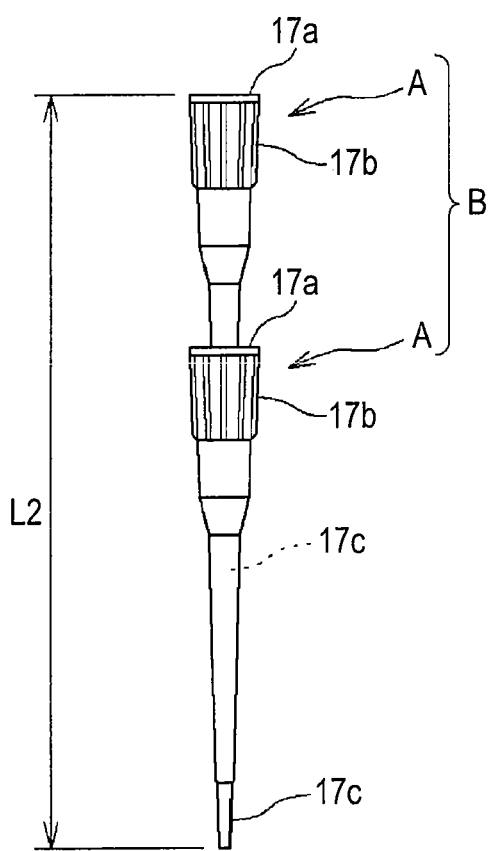
FIG. 3B is a diagram illustrating a pipette tip assembly.

FIG. 3A is a side view of a pipette tip A. The pipette tip A has an opening for ejecting a sample in the pipette tip A at a distal end 17c, and has an opening 17a at a proximal end. In addition, a body section 17b is a hollow tube connected to the opening 17a, and the other end (17c) has a tapered shape which is finer than that of the opening 17a (body section 17b). Therefore, as shown in FIG. 3B, a distal end 17c of one pipette tip A is inserted into an opening 17a of another pipette tip A, and thus a pipette tip assembly B can be obtained in which the pipette tips A, A are piled up.

A length L1 of one pipette tip A is about 53 mm, and a length L2 of a pipette tip assembly B formed of two pipette tips A, A is about 78 mm. In addition, the pipette tip assembly B is already formed at the time when a user inputs pipette tips A to an input port of the pipette tip supplying apparatus 13, or formed after the input. The pipette tip assembly B in this embodiment may be a pipette tip assembly in which three or more pipette tips A are piled up.

(3. Pipette Tip Supplying Apparatus 13)

Figure 4:
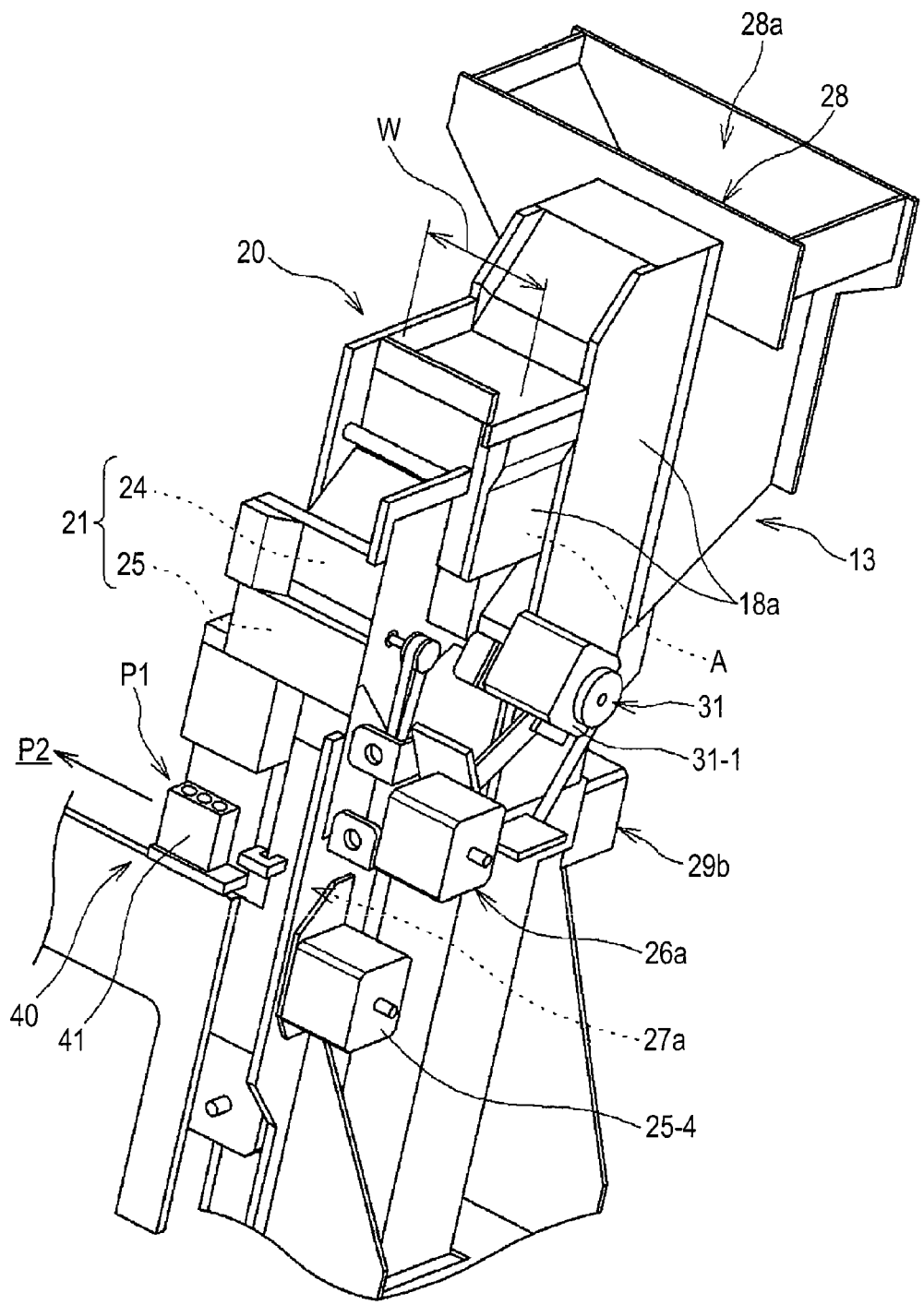
FIG. 4 is a perspective view of a pipette tip supplying apparatus.
Figure 5:
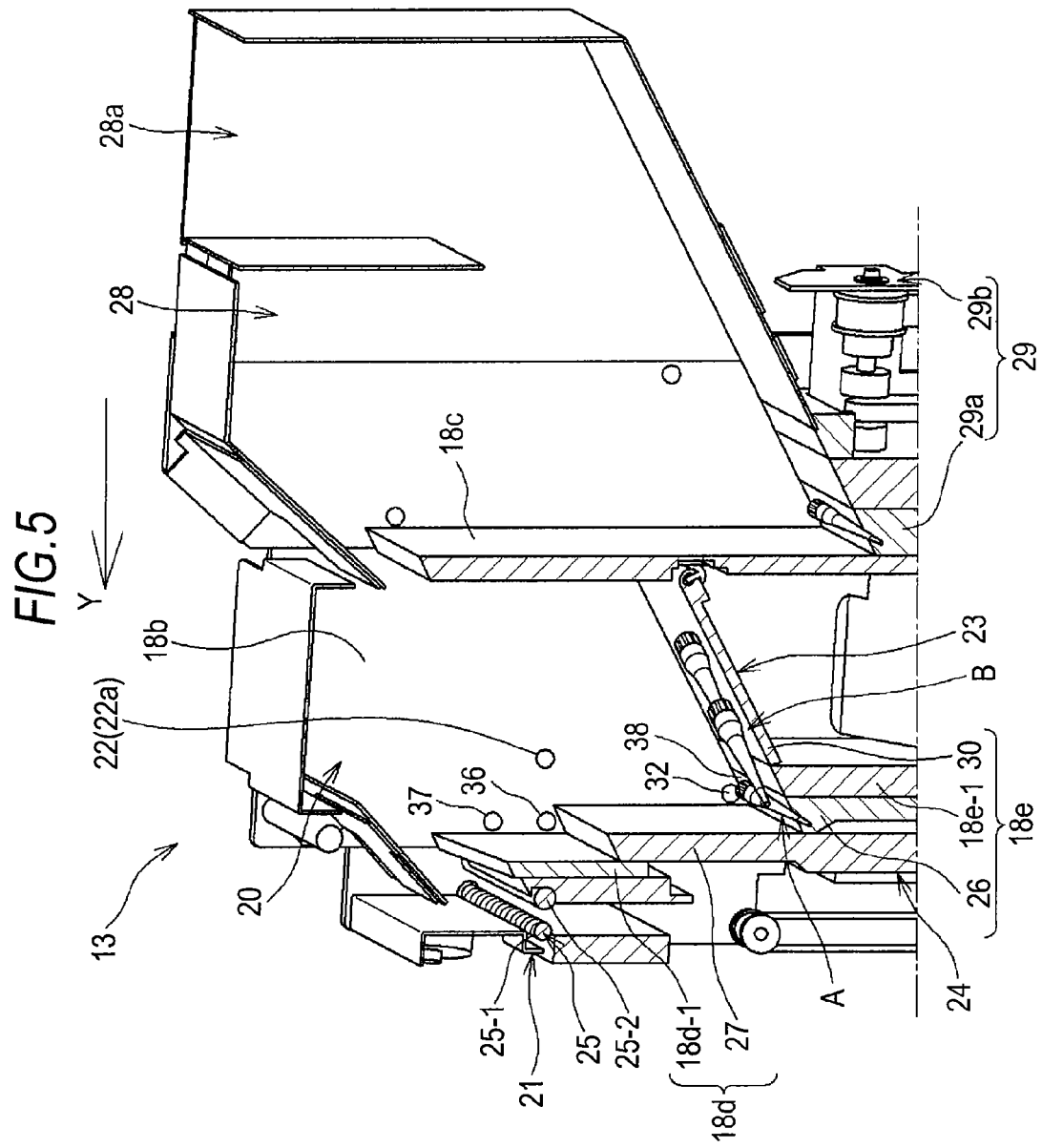
FIG. 5 is a perspective view of a part of the pipette tip supplying apparatus.

FIG. 4 is a perspective view of the pipette tip supplying apparatus 13. FIG. 5 is a perspective view of a part of the pipette tip supplying apparatus 13 and shows a state in which a part of a side wall 18a (see FIG. 4) is detached in order to illustrate the interior structure. The pipette tip supplying apparatus 13 is provided with a pipette tip input section 28 to which a plurality of pipette tips A are input by a user via an input port 28a, a pipette tip storing section 20 which stores a plurality of pipette tips A, a pipette tip carry-in section 29 for carrying pipette tips A stored in the pipette tip input section 28 in the pipette tip storing section 20, and a pipette tip supplying section 21 which supplies pipette tips A in the pipette tip storing section 20 one by one to the first position P1 disposed outside the pipette tip storing section 20. Although will be described later, the pipette tip supplying section 21 has a tip lifting mechanism section 24 and a tip transfer mechanism section 25.

In addition, in the pipette tip supplying apparatus 13, a direction in which a pipette tip A is fed to the pipette tip storing section 20 from the pipette tip input section 28 (direction of the arrow Y in FIG. 5) is set as a forward-backward direction, and a horizontal direction perpendicular to the forward-backward direction is set as a rightward-leftward direction. The rightward-leftward direction in the pipette tip storing section 20 is set as the width direction of the pipette tip storing section 20.

In FIG. 5, the pipette tip supplying apparatus 13 is provided with the detector 22 which detects whether or not a pipette tip assembly B is present in the pipette tip storing section 20, and a pipette tip discharging section 23 for discharging a pipette tip assembly B in the pipette tip storing section 20 to the outside of the pipette tip storing section 20. When the detector 22 detects a pipette tip assembly B, the CPU 401a of the controller 4 controls the pipette tip discharging section 23 so that the pipette tip assembly B is discharged from the pipette tip storing section 20.

The detector 22 of this embodiment is formed of a sensor having a light-emitting element and a light-receiving element. In addition, the pipette tip discharging section 23 of this embodiment has a rectangular plate-shaped discharging plate 30 which constitutes a part of the bottom of the pipette tip storing section 20, and a discharge driving section 31 (see FIG. 4) which drives the discharging plate 30.

As shown in FIG. 5, the pipette tip storing section 20 has a space surrounded by a side wall 18b on the right side, the side wall 18a on the left side (side wall omitted in FIG. 5), a rear wall 18c, a front wall 18d, and a bottom section 18e, and in this space, a plurality of pipette tips A can be stored. An upper surface of the bottom section 18e is constituted of an upper surface of the discharging plate 30 of the pipette tip discharging section 23, an upper surface of a fixed bottom member 18e-1 which is fixed to the apparatus, and an upper surface 38 of a first lifting member 26 positioned at the lower limit position. A bottom surface of the pipette tip storing section 20 is inclined so as to be lower toward the front wall 18d. Therefore, a pipette tip A input to the pipette tip storing section 20 can be put on the upper surface of the first lifting member 26 by its own weight. Although will be described later, the first lifting member 26 is a member which can be moved in the vertical direction. The front wall 18d is constituted of a second lifting member 27 and a fixed wall member 18d-1 which is fixed to the apparatus. Although will be described later, the second lifting member 27 is a member which can be moved in the vertical direction.

The members constituting the rear wall 18c, the front wall 18d and the bottom section 18e, respectively, are disposed between the right and left side walls 18a and 18b, and the width of each of the members in the rightward-leftward direction is set as a dimension W (see FIGS. 4 and 17) which is the same as the width of the pipette tip storing section 20 in the rightward-leftward direction. In addition, as shown in FIG. 17, the dimension W is greater than a length L1 in the longitudinal direction of a single pipette tip A and is less than a length L2 in the longitudinal direction of a pipette tip assembly B in which two pipette tips A, A are piled up. Therefore, as shown in FIG. 5, a single pipette tip A lies on the bottom section 18e so that the longitudinal direction thereof coincides with the right-to-left width direction of the pipette tip storing section 20. A pipette tip assembly B is put on the bottom section 18e so that the longitudinal direction thereof does not coincide with but is oblique to the right-to-left width direction of the pipette tip storing section 20.

In addition, the pipette tip input section 28 is adjacent to the pipette tip storing section 20 with the rear wall 18c sandwiched therebetween. The pipette tip input section 28 is a section to which a plurality of pipette tips A are input by a user and which has a larger volume than the pipette tip storing section 20 and a larger storage capacity for pipette tips A than the pipette tip storing section 20. The input port 28a to which a pipette tip A is input is provided in an upper section of the pipette tip input section 28.

In addition, the pipette tip carry-in section 29 has a plate-shaped carry-in lifting member 29a which can be moved in the vertical direction, and a carry-in driving section 29b which drives the carry-in lifting member 29a up and down. An upper surface of the carry-in lifting member 29a constitutes a part of a bottom surface of the pipette tip input section 28 and can put a plurality of pipette tips A on the upper surface thereof, and the bottom surface of the pipette tip input section 28 is inclined so as to be lower toward the pipette tip storing section 20. Therefore, a pipette tip A input to the pipette tip input section 28 can be put on the upper surface of the carry-in lifting member 29a by its own weight. The specific configuration of the carry-in driving section 29b is the same as that of a first lifting driving section 26a to be described later (see FIG. 7), and herein, the description thereof will be omitted.

By driving the carry-in driving section 29b and elevating the carry-in lifting member 29a, the pipette tip A put on the upper surface of the carry-in lifting member 29a is carried in the pipette tip storing section 20 over the rear wall 18c. The driving of the carry-in driving section 29b is based on a control signal from the controller 4.

According to the pipette tip input section 28 and the pipette tip carry-in section 29, many pipette tips A can be stored in the pipette tip input section 28 in advance, and by inputting a predetermined amount of pipette tips A to the pipette tip storing section 20 by the pipette tip input section 29 at a predetermined time, the number of the pipette tips A in the pipette tip storing section 20 can be maintained to be smaller than in the pipette tip input section 28. Therefore, although will be described later, the pipette tip assembly B can be more accurately detected in the pipette tip storing section 20.

With the tip transfer mechanism section 25, the tip lifting mechanism section 24 has a function for supplying pipette tips A which are stored in the pipette tip storing section 20 one by one to the first position P1 disposed outside the pipette tip storing section 20 as described above. The tip lifting mechanism section 24 has the first lifting member 26 which can be moved in the vertical direction, and the first lifting driving section 26a (see FIG. 4) which drives the first lifting member 26 up and down. The first lifting member 26 is a rectangular plate-shaped member which is long in the vertical direction, and the width direction thereof is provided in the width direction of the pipette tip storing section 20. In addition, the first lifting member 26 has the upper surface 38 on which a single pipette tip A is put in a state in which the longitudinal direction thereof is in the width direction of the pipette tip storing section 20. Therefore, a pipette tip A stored in the pipette tip storing section 20 can be put on the upper surface 38 and lifted in a state in which the longitudinal direction thereof coincides with the width direction of the pipette tip storing section 20. At this time, the pipette tip A is elevated (guided) along the vertical surface of the second lifting member 27.

Furthermore, the tip lifting mechanism section 24 has the second lifting member 27 which can be moved in the vertical direction and a second lifting driving section 27a (see FIG. 4) which drives the second lifting member 27 up and down in order to receive and put a pipette tip A which is lifted up to a predetermined height by the first lifting member 26 on the upper surface and to further lift the pipette tip A. The second lifting member 27 is a rectangular plate-shaped member which is long in the vertical direction, and the width direction thereof is provided in the width direction of the pipette tip storing section 20. In addition, the second lifting member 27 has an upper surface on which a single pipette tip A is put in a state in which the longitudinal direction thereof is in the width direction of the pipette tip storing section 20. Therefore, a pipette tip A can be put on the upper surface and lifted in a state in which the longitudinal direction thereof coincides with the width direction of the pipette tip storing section 20. On the upper surface of the second lifting member 27, only one pipette tip A can be put, and the pipette tip A is elevated along the vertical surface of the fixed wall member 18*d*-1.

In addition, as described above, a single pipette tip A is put on the upper surface 38 of the first lifting member 26 in the bottom section 18*e* so that the longitudinal direction thereof coincides with the right-to-left width direction of the pipette tip storing section 20 (see FIG. 5). The upper surface 38 of the first lifting member 26 which is in the lowest place is flush with the upper surface of the discharging plate 30 and is inclined downward toward the second lifting member 27. When the first lifting member 26 is elevated by the driving of the first lifting driving member 26*a*, the single pipette tip A is lifted, and when the pipette tip A arrives at a height (upper limit position of the first lifting member 26) of the upper surface of the second lifting member 27 positioned at the lower limit position, the pipette tip A is transferred to the upper surface of the second lifting member 27 by its own weight. The upper surface of the second lifting member 27 is inclined as the upper surface 38 of the first lifting member 26.

When the second lifting member 27 is elevated up to the upper limit position by the driving of the second lifting driving member 27*a*, the pipette tip A put on the upper surface thereof is supplied to the tip transfer mechanism section 25 over the fixed wall member 18*d*-1. The driving of the first and second lifting driving sections is based on a control signal from the controller 4.

In addition, the pipette tip storing section 20 is provided with a detector 36 (sixth detector 36) which detects whether or not a pipette tip A is present on the upper surface of the second lifting member 27 positioned at the lower limit position. The detector 36 is an optical sensor as in the case of the first detector 22. With the blocking of the light to the light-receiving element from the light-emitting element by the pipette tip, the detector 36 can detect whether or not a pipette tip A is present on the upper surface of the second lifting member 27 positioned at the lower limit position.

Furthermore, the pipette tip storing section 20 is provided with a detector 37 (seventh detector 37) for detecting whether or not a plurality of pipette tips A are present on the upper surface of the second lifting member 27. The detector 37 is an optical sensor as in the case of the first detector 22. By detecting a pipette tip at a predetermined position (position at which the light to the light-receiving element from the light-emitting element is blocked by the pipette tip only when a plurality of pipette tips are put on the second lifting member 27) in the course of the elevation of the second lifting member 27, the detector 37 can detect the presence of a plurality of pipette tips A on the upper surface of the second lifting member 27. The presence of the pipette tips A can be determined by the CPU 401*a* of the controller 4 receiving the signals from the detectors 36 and 37.

Figure 6:
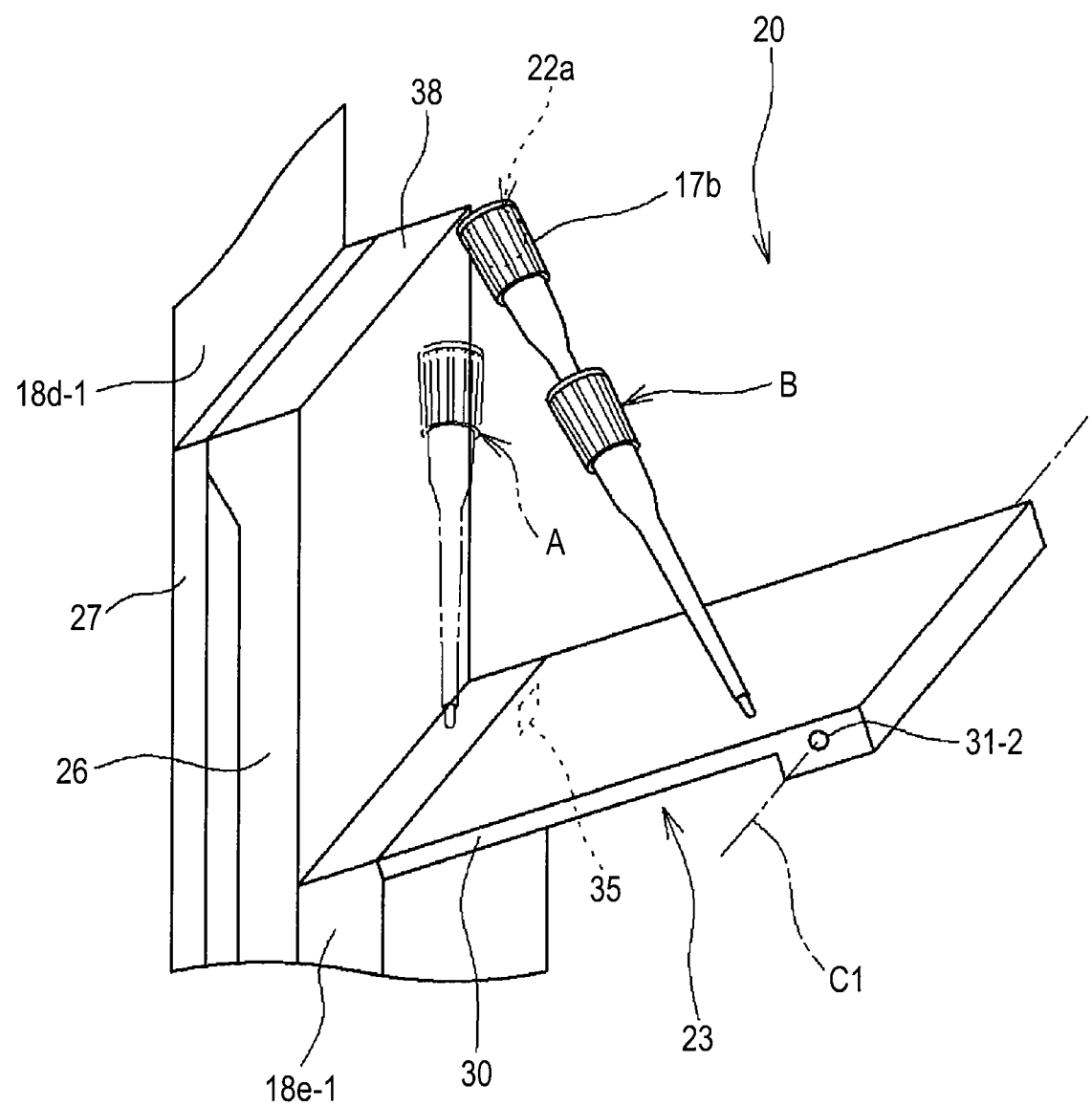
FIG. 6 is a diagram illustrating the inside of a pipette tip storing section.

On the other hand, as shown in FIG. 5, a pipette tip assembly B is put on the bottom section 18*e* so that the longitudinal direction thereof does not coincide with but is oblique to the right-to-left width direction of the pipette tip storing section 20 as described above. Therefore, even when the first lifting member 26 is elevated, the entire pipette tip assembly B is not transported upward, and as shown in FIG. 6, only a part thereof (in this embodiment, body section 17*b* of one pipette tip A) is raised and thus the entire pipette tip assembly is erected.

The specific configurations of the first lifting driving section 26*a* and the second lifting driving section 27*a* will be described using FIG. 7. The configurations of both of the driving sections 26*a* and 27*a* are the same as each other, and thus the first lifting driving section 26*a* will be described as a representative.

The first lifting driving section 26*a* has a motor 26*a*-1 which can be rotated positively and reversely, a driving pulley 26*a*-2 which is rotated by the motor 26*a*-1, a driven pulley 26*a*-3 which is provided to be distant from the driving pulley 26*a*-2 in the vertical direction, a belt 26*a*-4 which is built between both of the pulleys 26*a*-2 and 26*a*-3, and a connecting member 26-5 which is connected and fixed to the belt 26*a*-4 and the first lifting member 26.

Figure 7:
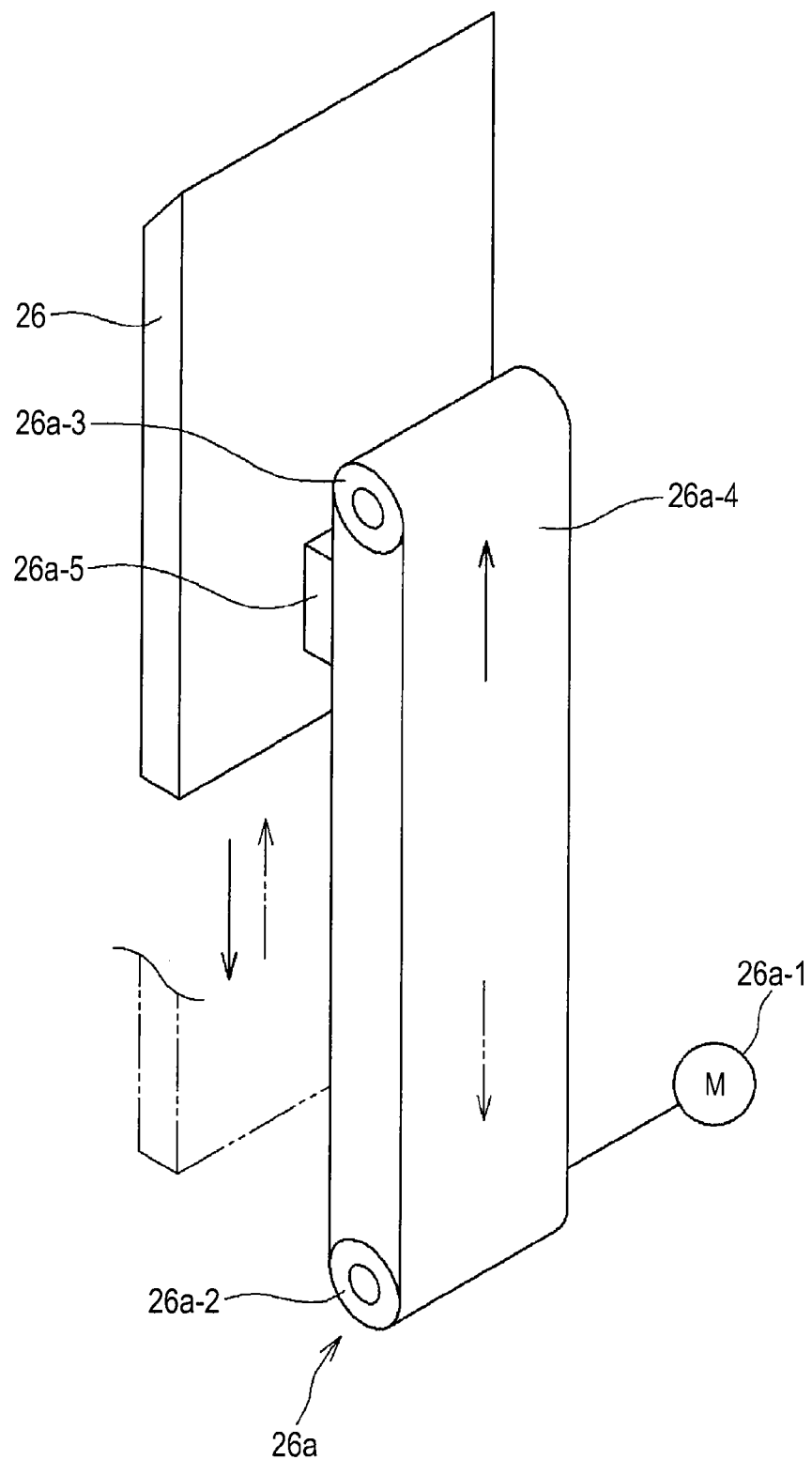
FIG. 7 is a diagram illustrating a first lifting driving section.

The motor 26*a*-1 has a decelerator section (not shown), and when the motor 26*a*-1 rotates in one direction, the belt 26*a*-4 rotates in one direction (solid line arrow in FIG. 7). Accordingly, the first lifting member 26 can be moved down. On the other hand, when the motor 26*a*-1 rotates in the other direction, the belt 26*a*-4 rotates in the other direction (dashed line arrow in FIG. 7). Accordingly, the first lifting member 26 can be elevated. The driving of the motor 26*a*-1 is based on a control signal from the controller 4.

In FIG. 5, the light-emitting element and the light-receiving element of the first detector 22 are provided in the right and left side walls 18*a* and 18*b* in order to detect a pipette tip assembly B present in the pipette tip storing section 20, and in this embodiment, with the blocking of the light to the light-receiving element from the light-emitting element by a part of the pipette tip assembly B, the detector 22 can detect the presence of the pipette tip assembly B. The determination of the presence can be performed by the CPU 401*a* of the controller 4 receiving a signal from the detector 22.

The position of the light-emitting element 22*a* will be described using FIG. 6. The light-emitting element 22*a* is positioned to be able to detect a pipette tip assembly B when one end of the pipette tip assembly B is raised by the lifting operation by the first lifting member 26. Specifically, the light-emitting element 22*a* is at a position which is higher than a single pipette tip A which is erected along the vertical line in the pipette tip storing section 20 by the operation of the first lifting member 26, and is disposed at a lower position than a pipette tip assembly B which is erected along the vertical line in the pipette tip storing section 20 by the operation of the first lifting member 26. In addition, the light-emitting element 22*a* is disposed on the upstream side of the first lifting member 26 in the direction in which the pipette tip in the pipette tip storing section 20 moves (direction of the arrow Y in FIG. 5). Accordingly, the detector 22 can securely detect the pipette tip assembly erected by the operation of the first lifting member 26, and by opening the discharging plate 30, the pipette tip assembly positioned on the discharging plate 30 can be easily discharged to the outside of the pipette tip storing section 20. The light-receiving element is at the same height as the light-emitting element 22*a* and is provided at a position opposed to the light-emitting element 22*a*.

By providing the light-emitting element 22*a* and the light-receiving element at the positions, respectively, a pipette tip A cannot be detected in a state in which the single pipette tip A is erected in the pipette tip storing section 20. In a state in which a pipette tip assembly B is erected along the vertical line in the pipette tip storing section 20 or erected in an oblique direction (state in FIG. 6), the pipette tip assembly B is detected. That is, it is possible to suppress erroneously detecting the single pipette tip A as the pipette tip assembly B.

In addition, as shown in FIG. 5, the pipette tip supplying apparatus 13 is provided with the second detector 32 which detects a single pipette tip A which is officially put on the upper surface 38 of the first lifting member 26. The "officially" means a state in which a pipette tip A is put on the upper surface 38 so that the longitudinal direction of the pipette tip A coincides with the right-to-left width direction of the first lifting member 26 (pipette tip storing section 20). The second detector 32 is an optical sensor as in the case of the first detector 22. With the blocking of the light to the light-receiving element from the light-emitting element by the pipette tip, the second detector 32 can detect the presence of the pipette tip A. The determination of the presence can be performed by the CPU 401a of the controller 4 receiving a signal from the detector 32.

Figure 8:
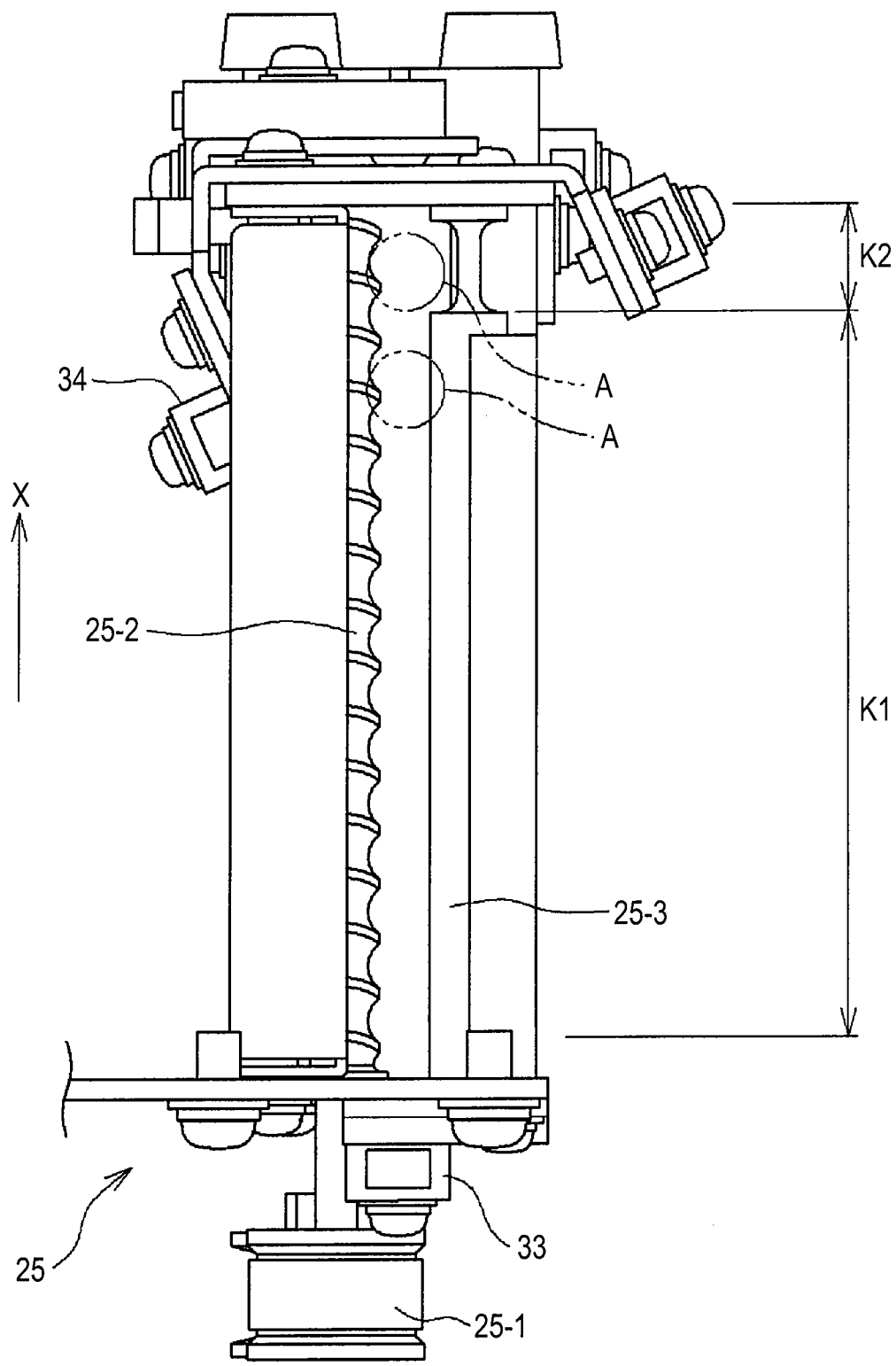
FIG. 8 is a plan view of a tip transfer mechanism section.

The tip transfer mechanism section 25 has a function for supplying pipette tips A which are supplied by the tip lifting mechanism section 24 one by one to the first position P1 (see FIG. 4) disposed outside the pipette tip storing section 20. As shown in FIG. 8, the tip transfer mechanism section 25 has a pulley 25-1, a rotation shaft 25-2 which is rotated by the pulley 25-1, a guide member 25-3 which is long in the rightward-leftward direction and is provided to be parallel to the rotation shaft 25-2 with an interval therebetween in the forward-backward direction, and a motor 25-4 (see FIG. 4) which rotates the pulley 25-1. The rotation shaft 25-2 has a screw-shaped groove formed thereon.

As described above, when a pipette tip A put on the upper surface of the second lifting member 27 climbs over the fixed wall member 18d-1 due to the elevation of the second lifting member 27 (see FIG. 5), the pipette tip A is dropped between the rotation shaft 25-2 and the guide member 25-3. Therefore, since the center of the pipette tip A is positioned closer to the distal end section 17c than the body section 17b, the distal end section 17c hangs downward, and thus the body section 17b is supported between the rotation shaft 25-2 and the guide member 25-3 and the pipette tip A is fitted in the screw groove of the rotation shaft 25-2.

When the pulley 25-1 is rotated, the pipette tip A can be moved to one side (upper side in FIG. 8) in the rightward-leftward direction along the screw groove (arrow X). Between the rotation shaft 25-2 and the guide member 25-3, a first region K1 which is narrower than the body section 17b of the pipette tip A and a second region K2 which is wider than the body section 17b are provided, and when the pipette tip A arrives at the second region K2, the pipette tip A can be dropped to the first position P1 (see FIG. 4) by its own weight.

In addition, the tip transfer mechanism section 25 is provided with a third detector 33 and a fourth detector 34. The third detector 33 and the fourth detector 34 are optical sensors as in the case of the detectors 22 and 32. With the blocking of the light to the light-receiving element from the light-emitting element by the pipette tip, the third detector 33 and the fourth detector 34 can detect the presence of the pipette tip A. The third detector 33 detects whether or not a pipette tip A is present between the rotation shaft 25-2 and the guide member 25-3. The fourth detector 34 detects whether or not a pipette tip A is present at a position immediately before the second region K2 in the first region K1. The determination of the presence of a pipette tip A can be performed by the CPU 401a of the controller 4 receiving signals from the detectors 33 and 34.

As shown in FIG. 6, the pipette tip discharging section 23 has the rectangular plate-shaped discharging plate 30 which constitutes a part of the bottom of the pipette tip storing section 20 and the discharge driving section 31 (see FIG. 4) which drives the discharging plate 30. The discharging plate 30 is attached to the rear wall 18c of the pipette tip storing section 20 around a central line C1 of the horizontal axis to be able to be oscillated. The discharge driving section 31 has a motor 31-1 (see FIG. 4) which can be rotated positively and reversely, and an operation shaft 31-2 (see FIG. 6) which operates simultaneously with the rotation of the motor 31-1, and the discharging plate 30 rotates integrally with the operation shaft 31-2.

Figure 9:
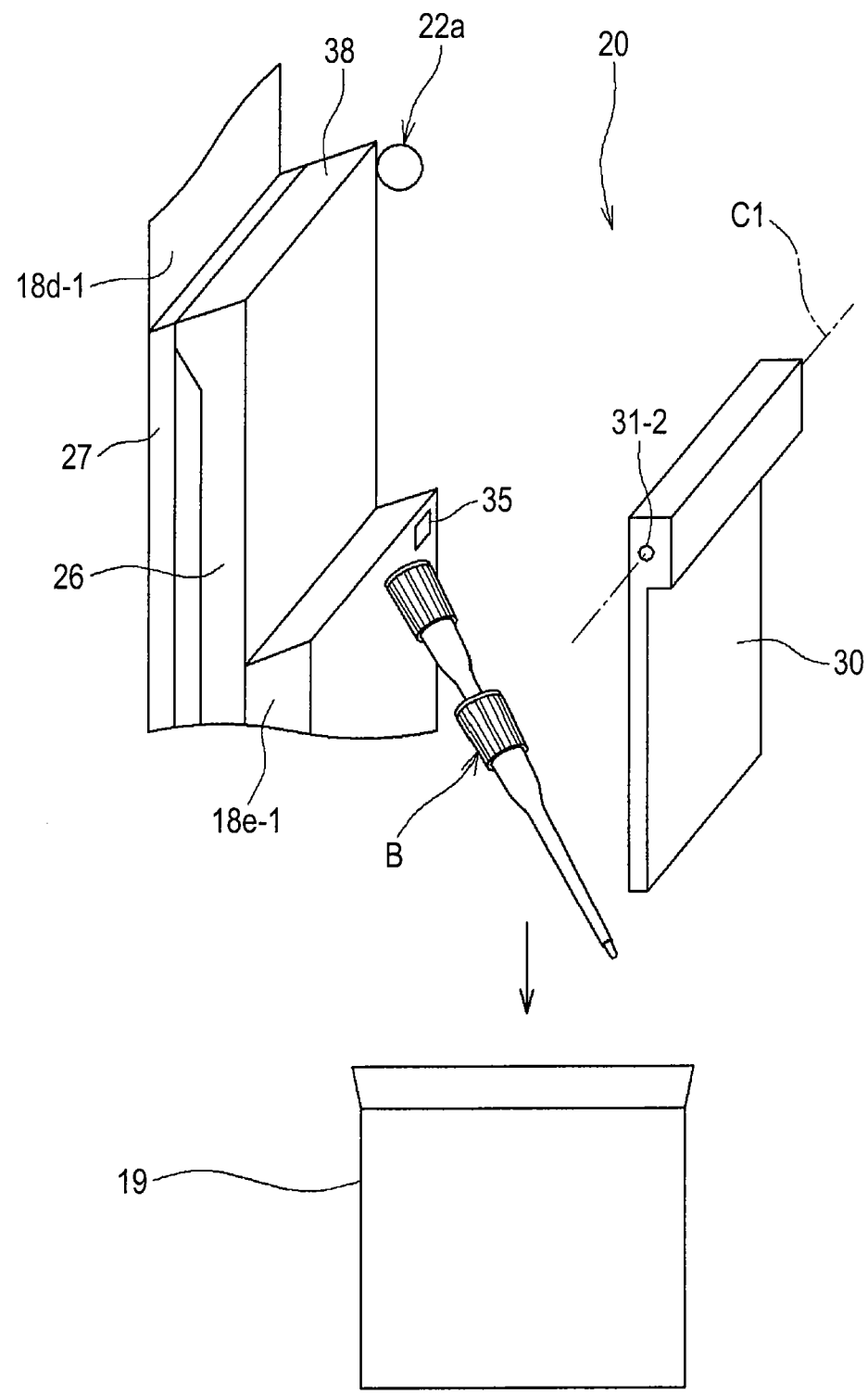
FIG. 9 is a diagram illustrating the inside of the pipette tip storing section.

When the motor 31-1 rotates in one direction, the discharging plate 30 which has closed the bottom of the pipette tip storing section 20 as shown in FIG. 6 opens the bottom as shown in FIG. 9. Accordingly, a pipette tip assembly B present in the pipette tip storing section 20 is dropped from the pipette tip storing section 20, and can be discharged from the pipette tip storing section 20. In this manner, the discharging plate 30 of the pipette tip discharging section 23 constitutes a part of the bottom section of the pipette tip storing section 20 and is provided to be able to partially open the bottom section downward. The motor 31-1 operates on the basis of a control signal from the controller 4, and the controller 4 opens the bottom section of the pipette tip storing section 20 by the pipette tip discharging section 23 and thus can discharge a pipette tip assembly B from the bottom section of the pipette tip storing section.

When the motor 31-1 rotates in the other direction from the state in which the bottom is opened as shown in FIG. 9, the discharging plate 30 returns a state of closing the bottom of the pipette tip storing section 20. In addition, the pipette tip discharging section 23 is provided with a fifth detector 35, and the fifth detector 35 can detect whether or not the discharging plate 30 is in a complete close state. The fifth detector 35 may be a noncontact sensor (optical sensor) as in the case of the above-described detectors, or may be a contact limit sensor. The determination of the close state can be performed by the CPU 401a of the controller 4 receiving a signal from the detector 35.

As described above, the discharging plate 30 of the pipette tip discharging section 23 is provided to be able to partially open the bottom section of the pipette tip storing section 20, and is inclined downward toward the upper surface 38 of the first lifting member 26. Therefore, the pipette tip A which is carried in the pipette tip storing section 20 can be moved to the upper surface 38 of the first lifting member 26 by its weight. Meanwhile, as described above, the widths of the pipette tip storing section 20 and the first lifting member 26 in the rightward-leftward direction are smaller than the length of a pipette tip assembly B in the longitudinal direction, and thus the entire pipette tip assembly B can be positioned to lie on the discharging plate 30, not on the upper surface 38 of the first lifting member 26. Therefore, with the operation of discharging a pipette tip assembly B by the pipette tip discharging section 23, the pipette tip assembly B is discharged below the pipette tip storing section 20, but it is possible to suppress a single pipette tip A put on the upper surface 38 of the first lifting member 26 from being discharged.

As shown in FIG. 9, the pipette tip supplying apparatus 13 is provided with an receiving section 19 for receiving a pipette tip assembly B which is discharged by the pipette tip discharging section 23 at a position below the bottom section of the pipette tip storing section 20. The receiving section 19 of this embodiment is a box which accommodates waste materials such as used pipette tips A and cuvettes. In this case, the receiving section 19 is used for pipette tip assemblies B and waste materials alike. The receiving section 19 may be dedicated for pipette tip assemblies, and in this case, the discharged pipette tip assembly B may be separated into single pipette tips A, A and then may be input again to the input port 28a (see FIG. 4).

(4. Pipette Tip Supplying Method)

A pipette tip supplying method which is performed by the pipette tip supplying apparatus 13 configured as described above will be described. In the following supplying method, a process in which the main agent is not particularly described is a process which is performed by the CPU 401a of the controller 4.

In FIG. 5, when many pipette tips A are input to the pipette tip input section 28 by a user and the pipette tips A are stored in the pipette tip input section 28, the carry-in lifting member 29a is elevated and a pipette tip A put on the upper surface thereof is carried in the pipette tip storing section 20. The carrying-in is repeatedly performed at a predetermined time, and in the pipette tip storing section 20, a smaller number of pipette tips A than the pipette tip input section 28 are stored. At this time, a pipette tip assembly B may be present in the pipette tip storing section 20. A single pipette tip A rolls down to the upper surface 38 of the first lifting member 26 by the inclined bottom surface of the pipette tip storing section 20.

Figure 10:
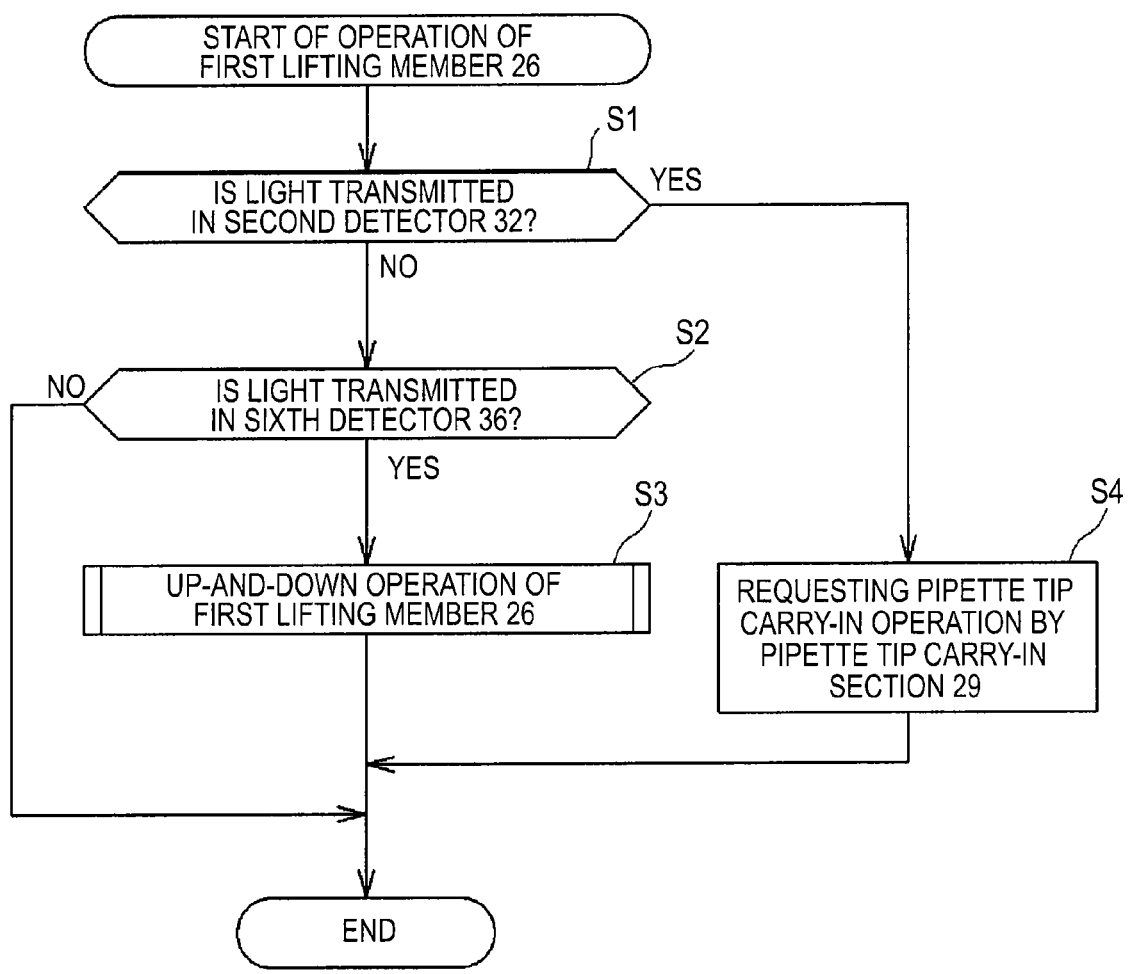
FIG. 10 is a flow diagram illustrating an operation of a first lifting member.

FIG. 10 is a flow diagram illustrating an operation of a first lifting member 26. First, the first lifting member 26 is at the lower limit position (in the state in FIG. 5). In this state, the CPU 401a determines whether or not a pipette tip A is present on the upper surface 38 of the first lifting member 26 positioned at the lower limit position on the basis of a signal from the second detector 32 (Step S1 in FIG. 10). When the light is shielded between the light-emitting element and the light-receiving element of the second detector 32 and it is determined that the pipette tip A is present (No in Step S1), the CPU 401a determines whether or not the pipette tip A is present on the upper surface of the second lifting member 27 positioned at the lower limit position on the basis of a signal from the sixth detector 36 (Step S2).

In this step S2, when the light is transmitted between the light-emitting element and the light-receiving element of the sixth detector 36 and it is determined that the pipette tip A is not present on the upper surface of the second lifting member 27 (Yes in Step S2), the up-and-down operation of the first lifting member 26 is started (Step S3). On the other hand, in Step S2, when the light is shielded between the light-emitting element and the light-receiving element of the sixth detector 36 and it is determined that the pipette tip A is present on the second lifting member 27 (No in Step S2), the first lifting member 26 does not perform the moving-up operation and is put on hold.

In Step S1, when the pipette tip A is not present on the upper surface 38 of the first lifting member 26 positioned at the lower limit position, it is thought that there is no pipette tip A in the pipette tip storing section 20. Therefore, the controller 4 receives a request for a carrying-in operation of the pipette tip A by the pipette tip carry-in section 29 (Step S4), and thus by an instruction signal from the controller 4, the carry-in lifting member 29a is elevated and a pipette tip A put on the upper surface thereof is carried in the pipette tip storing section 20.

Figure 11:
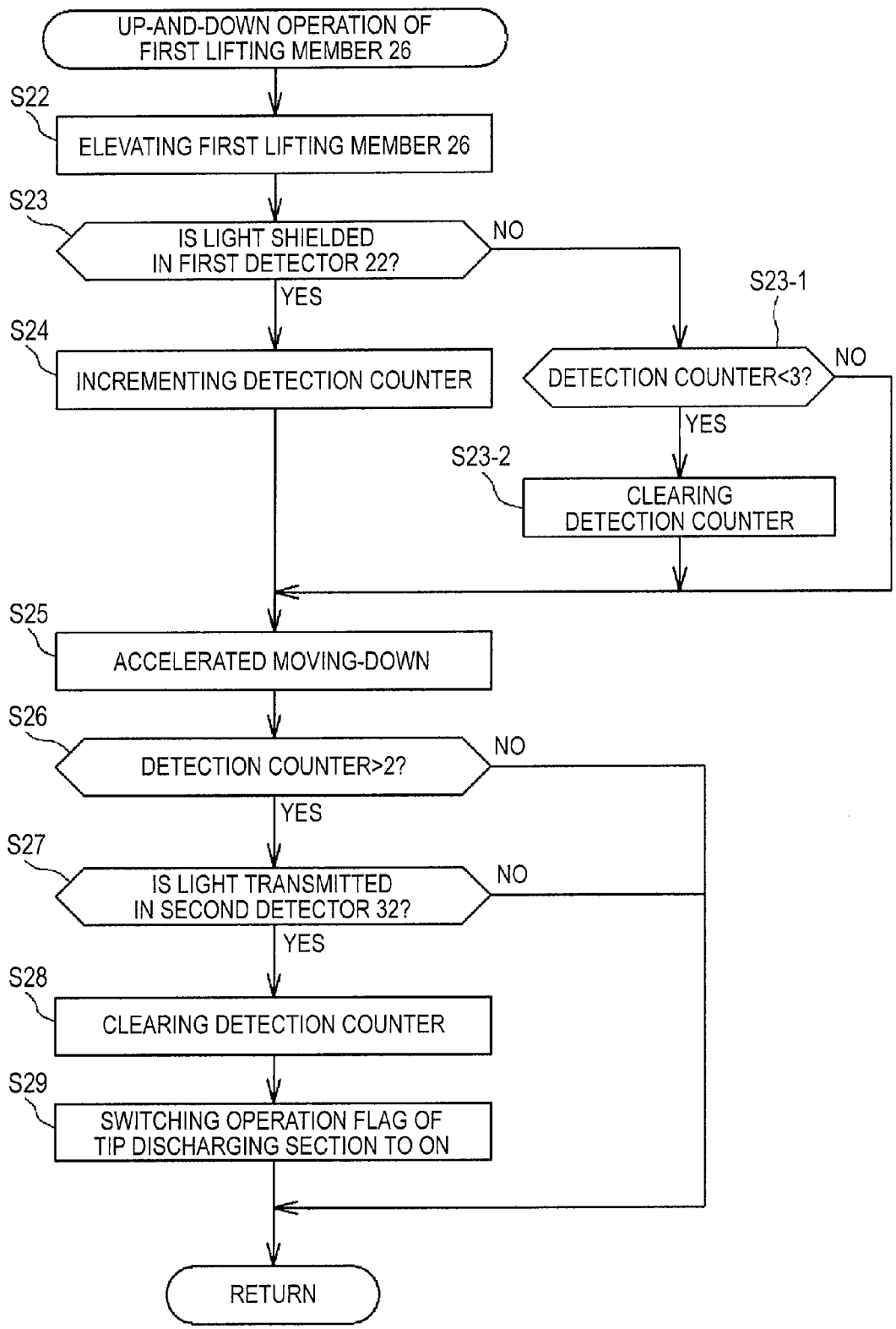
FIG. 11 is a flow diagram illustrating an up-and-down operation of the first lifting member.

In FIG. 11, when the up-and-down operation of the first lifting member 26 is started, the CPU 401a prompts the first lifting driving section 26a to operate to elevate the first lifting member 26 up to the upper limit position (Step S22). The CPU 401a determines the presence of the pipette tip assembly B in the pipette tip storing section 20 on the basis of a detection signal from the first detector 22 (Step S23). That is, it is determined whether the light is transmitted or shielded between the light-emitting element and the light-receiving element of the first detector 22. When the pipette tip B is present, the light is shielded (Yes in Step S23), a detection counter of the controller 4 is incremented (Step S24), and the first lifting member 26 is moved down up to the lower limit position (Step S25). The moving-down is performed with an increased acceleration speed in comparison to the case of the elevation. This is performed in hopes of separation of the pipette tip assembly B into single pipette tips A by the moving-down operation and the re-elevation operation (later Step S22) of the first lifting member 26.

In addition, the CPU 401a determines whether or not the detection counter counts 2 or higher (Step S26). Since the above-described Step S24 is a first-time operation, that is, the detection counter counts "1", the result is "No" in the determination in Step S26, the flow of FIG. 11 ends, and the process returns to the flow shown in FIG. 10.

When the up-and-down operation of the first lifting member 26 is restarted (Step S3 in FIG. 10), the first lifting member 26 is elevated up to the upper limit position (Step S22 in FIG. 11), and the presence of the pipette tip assembly B in the pipette tip storing section 20 is determined again on the basis of the detection result of the first detector 22 (Step S23). When the pipette tip assembly B is not eliminated and is still present, it is determined that the light is shielded (Yes in Step S23), the detection counter is incremented (Step S24), and the first lifting member 26 is moved down up to the lower limit position (Step S25). Therefore, the detection counter counts "2".

The result is "No" in the determination in Step S26, and thus the flow of FIG. 11 ends and the process returns to the flow shown in FIG. 10. In addition, when a third up-and-down operation of the first lifting member 26 is started (Step S3 in FIG. 10), Step S22 and Step S23 in FIG. 11 are performed. When the pipette tip assembly B is still present, the CPU 401a determines that the light is shielded (Yes in Step S23), the detection counter is incremented (Step S24), and the first lifting member 26 is moved down up to the lower limit position (Step S25). Therefore, the detection counter counts "3". Accordingly, the determination result is "Yes" in the determination in Step S26, and when confirming that the light is transmitted between the light-emitting element and the light-receiving element of the second detector 32 (Yes in Step S27), that is, when confirming that no pipette tip A is present on the first lifting member 26, the CPU 401a clears the detection counter (Step S28) and switches an operation flag of the pipette tip discharging section 23 to ON (Step S29).

As described above, in this embodiment, when the first detector 22 detects the pipette tip assembly B continuously a plural number of times (three times) with plural lifting operations (three times) of the first lifting member 26, the controller 4 performs the control to discharge the pipette tip assembly B from the pipette tip storing section 20 by the pipette tip discharging section 23. The reason for this is that the pipette tip assembly B may be separated into single pipette tips A due to the moving-down and lifting operation of the first lifting member 26 as described above. When the pipette tip assembly B is separated into single pipette tips, there is no need to perform the discharging operation, and it is possible to suppress the separated pipette tips A from being discharged by the pipette tip discharging section 23.

When the pipette tip assembly B is separated by the operation of the first lifting member 26 in the vertical direction, the determination result is "No" in Step S23, and when the detection counter counts less than 3 (Step S23-1), the detection counter is cleared (Step S23-2) and the process proceeds to Step S25.

Furthermore, in this embodiment, the second detector 32 is a sensor which can detect a single pipette tip A which is officially put on the upper surface 38 of the first lifting member 26. As described above, the CPU 401a of the controller 4 performs the discharging operation by the pipette tip discharging section 23 when the pipette tip assembly B is detected by the first detector 22 and no pipette tip A is detected by the second detector 32 in Step S27 (when the result is Yes in Step S27). The reason for this is to suppress, when the discharging operation is performed in the case in which a single pipette tip A is put on the first lifting member 26, the pipette tip A other than the pipette tip assembly B from being simultaneously discharged. That is, as in this embodiment, by performing the discharging operation when no pipette tip A is put on the first lifting member 26, other pipette tips A other than the pipette tip assembly B can be suppressed from being discharged together with the pipette tip assembly B.

Figure 12:
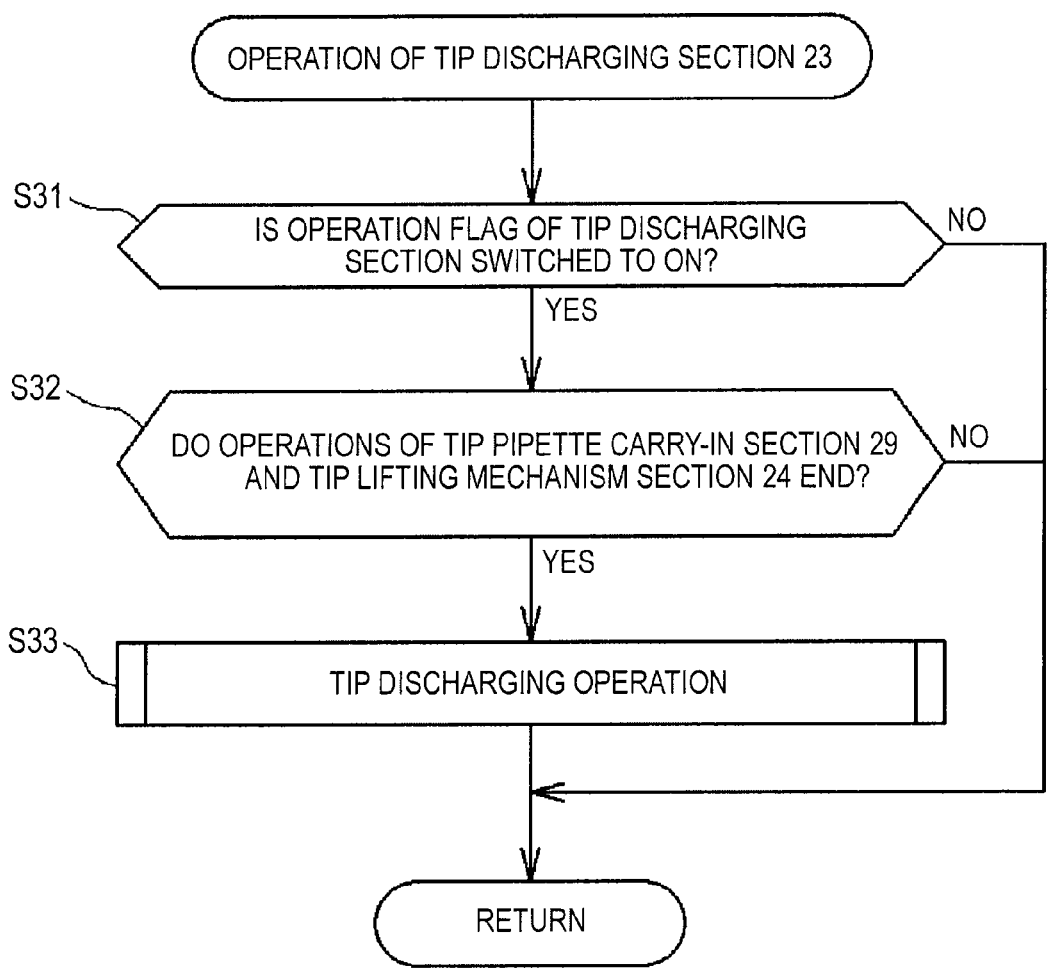
FIG. 12 is a flow diagram illustrating an operation of a pipette tip discharging section.

An operation of the pipette tip discharging section 23 will be described along FIG. 12. When confirming that the operation flag of the pipette tip discharging section 23 is switched to ON (Yes in Step S31), the CPU 401a determines whether or not the operation of the pipette tip carry-in section 29 and the operation of the tip lifting mechanism section 24 end (are stopped) (Step S32). When the operations end (are stopped) (Yes in Step S32), the CPU 401a performs a tip discharging operation (Step S33).

Figure 13:
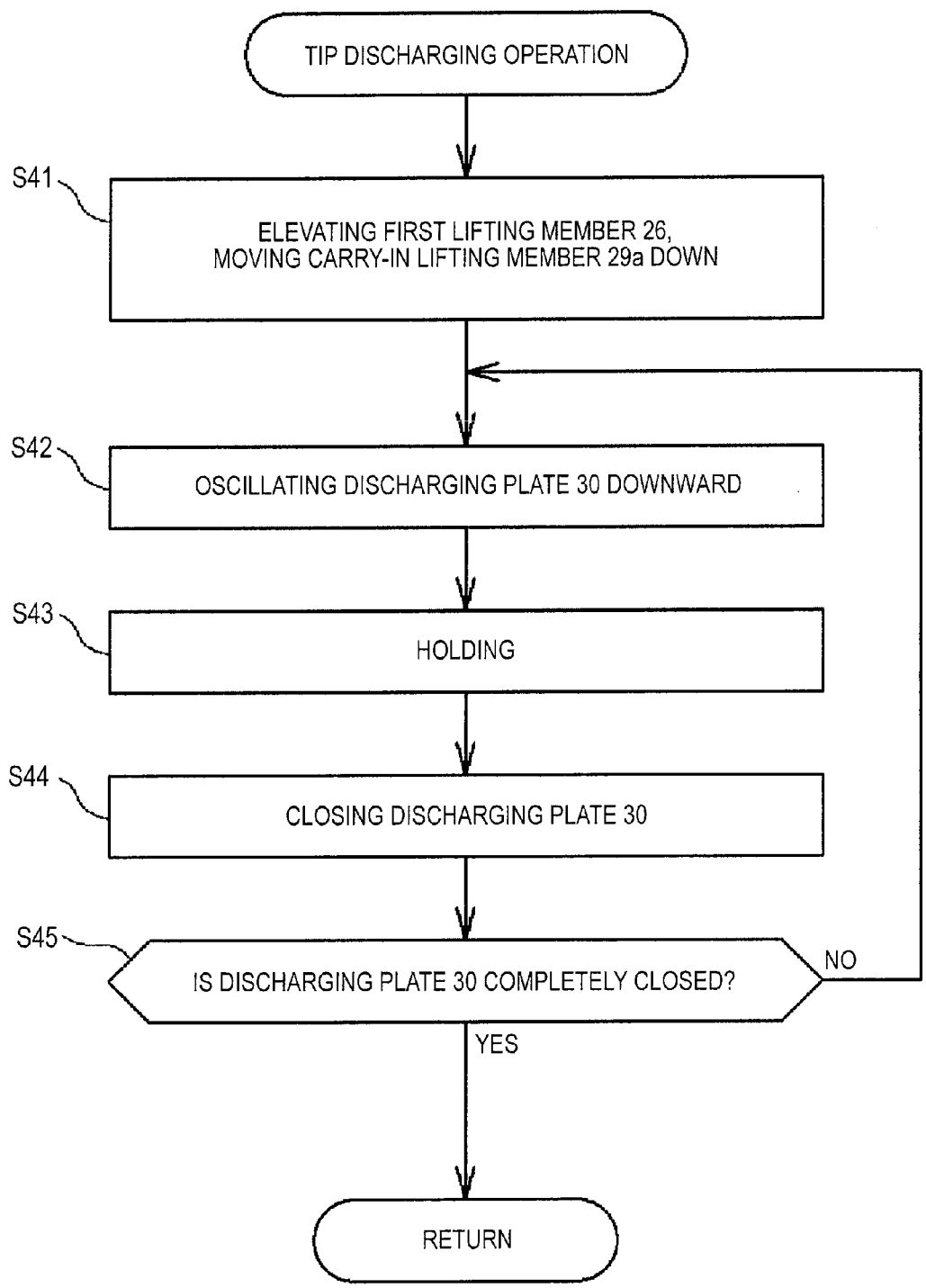
FIG. 13 is a flow diagram illustrating a tip discharging operation of the pipette tip discharging section.

FIG. 13 is a flow diagram of the tip discharging operation. First, the CPU 401a elevates the first lifting member 26 in order to easily drop the pipette tip assembly B, and moves the carry-in lifting member 29a downward so that a new pipette tip A is not carried in the pipette tip storing section 20 (Step S41). In addition, the CPU 401a oscillates the discharging plate 30 downward as shown in FIG. 9 to open the bottom section of the pipette tip storing section 20 (Step S42). Accordingly, the pipette tip assembly B present in the pipette tip storing section 20 is dropped. While oscillating the discharging plate 30 downward, the CPU 401a is put on hold for a predetermined time (Step S43), and then oscillates upward and closes the discharging plate 30 (Step S44).

The CPU 401a detects whether or not the discharging plate 30 is in a complete close state on the basis of a signal from the fifth detector 35 (Step S45). The reason for this is that when the pipette tip A (pipette tip assembly B) is caught in the discharging plate 30, the discharging plate 30 is not in a complete close state. When the discharging plate 30 is not in a complete close state (No in Step S45), the CPU 401a oscillates the discharging plate 30 downward again (Step S42). Therefore, even when a pipette tip assembly B is present in the pipette tip storing section 20, the pipette tip assembly B can be discharged to the outside of the pipette tip storing section 20.

When the elevation operation of the first lifting member 26 is started in a state in which the pipette tip A is put on the first lifting member 26 in the flow of FIG. 10 and the first lifting member 26 is elevated up to the upper limit position in the flow of FIG. 11 (Step S22), the pipette tip A is transferred onto the second lifting member 27.

Figure 14:
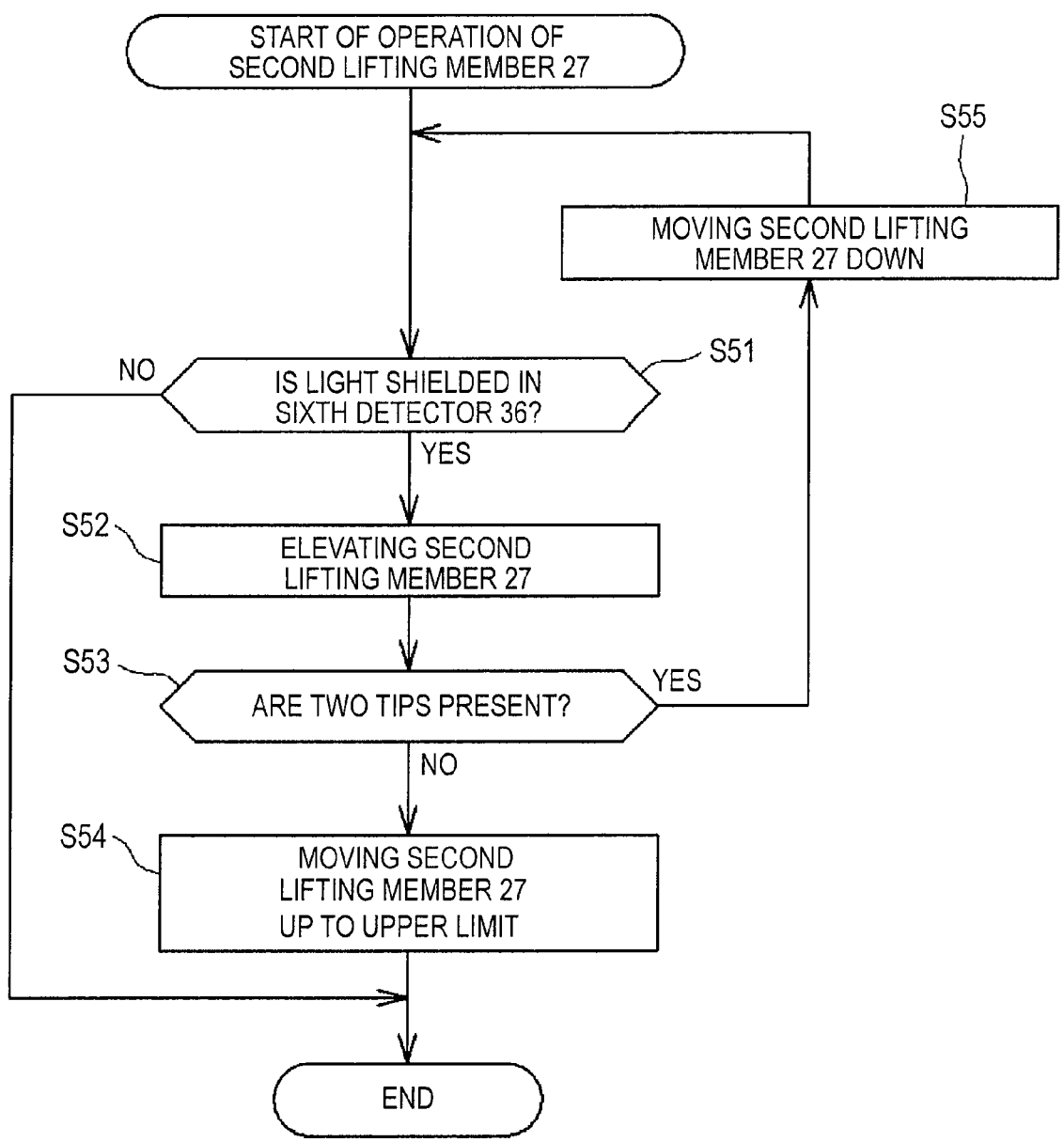
FIG. 14 is a flow diagram illustrating an operation of a second lifting member.

FIG. 14 is a flowchart showing an operation of the second lifting member 27. First, the CPU 401a determines whether or not the pipette tip A is present on the upper surface of the second lifting member 27 positioned at the lower limit position on the basis of a signal from the sixth detector 36 (Step S51 in FIG. 14). When it is determined that the light is shielded between the light-emitting element and the light-receiving element of the sixth detector 36 and the pipette tip A is present (when the result is Yes in Step S51), the second lifting member 27 is elevated (Step S52).

The CPU 401a determines whether or not a plurality of pipette tips A (two pipette tips) are present on the upper surface of the second lifting member 27 by the seventh detector 37 in the course of the elevation of the second lifting member 27 (Step S53). The reason for this is to prevent the plurality of pipette tips A from being collected and supplied to the next tip transfer mechanism section 25.

When the CPU 401a determines that a plurality of pipette tips A are present on the basis of a signal from the seventh detector 37 (Yes in Step S53), the second lifting member 27 is moved down up to the lower limit (Step S55), and the process returns to Step S51. In this manner, by moving the second lifting member 27 down, the pipette tips A on the second lifting member 27 are dropped to the bottom section of the pipette tip storing section 20, and thus only single pipette tips A are put on the second lifting member 27. On the other hand, when the CPU 401a determines that a plurality of pipette tips A are not present (No in Step S53), the second lifting member 27 is elevated up to the upper limit (Step S52) and the pipette tip A is supplied to the tip transfer mechanism section 25 over the fixed wall member 18d-1.

Figure 15:
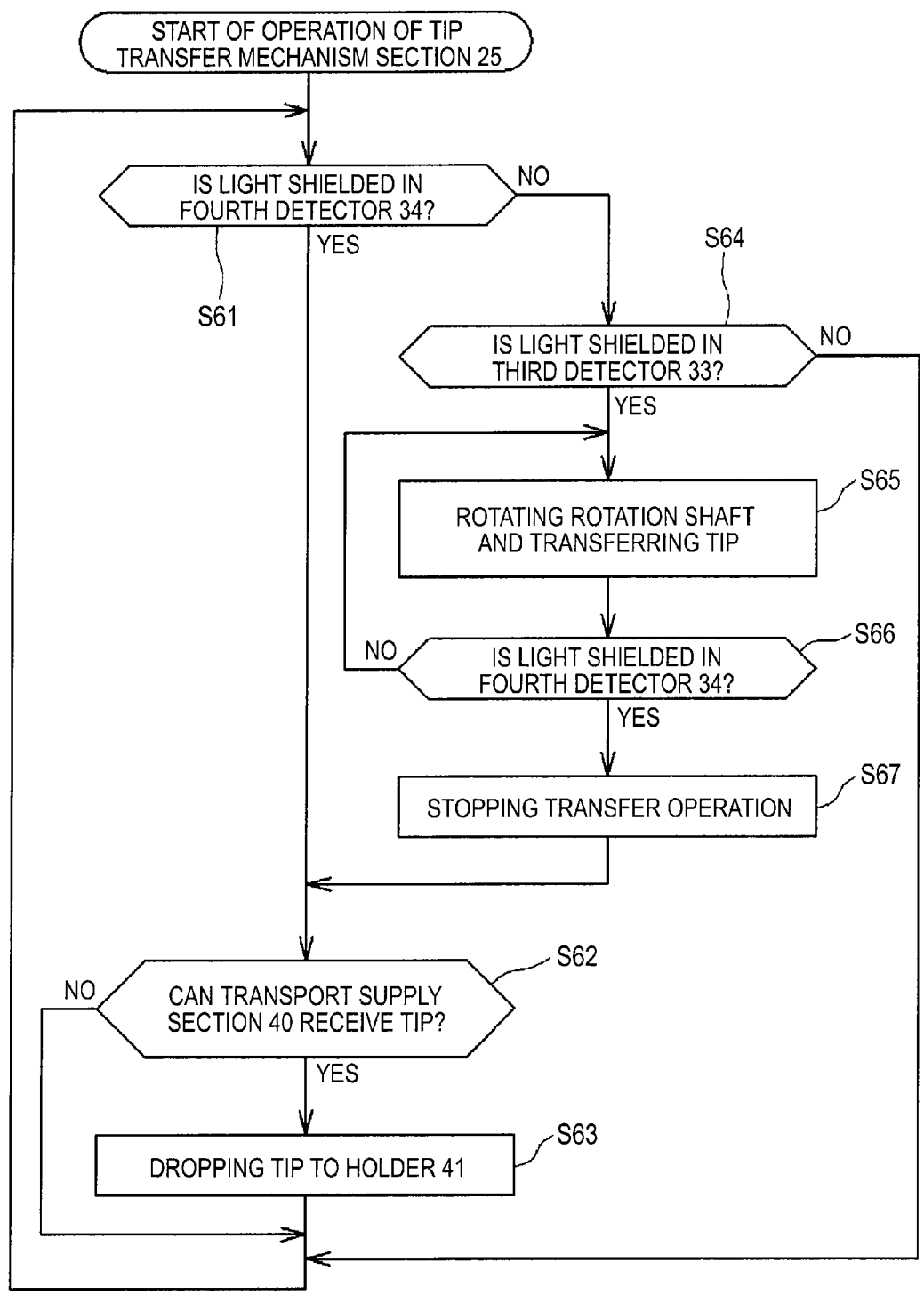
FIG. 15 is a flow diagram illustrating an operation of the tip transfer mechanism section.

An operation of the tip transfer mechanism section 25 will be described. In FIG. 15, the CPU 401a determines whether or not the pipette tip A is present at a position immediately before the second region K2 on the basis of a signal from the fourth detector 34 (see FIG. 8) (Step S61). The second region K2 is a region in which the pipette tip A can be dropped to the first position P1 (see FIG. 4). When it is determined that the pipette tip A is present (Yes in Step S61), the CPU 401a determines whether or not the transport supply section 40 can receive the pipette tip A (Step S62). As shown in FIG. 4, the holder 41 which receives the dropped pipette tip A is put on hold at the first position P1, and the CPU 401a determines whether the holder 41 can receive the pipette tip. When the holder 41 can receive the pipette tip, the CPU 401a rotates the rotation shaft 25-2 of the tip transfer mechanism section 25 in FIG. 8 to drop the pipette tip A present at the position immediately before the second region K2 from the second region K2 (Step S63). The dropped pipette tip is received by the holder 41.

In Step S61, when determining that no pipette tip A is present (No in Step S61), the CPU 401a determines whether or not the pipette tip A is present between the rotation shaft 25-2 and the guide member 25-3 on the basis of the detection result of the third detector 33 (See FIG. 8) (Step S64). When it is determined that the pipette tip A is present (Yes in Step S64), the CPU 401a rotates the rotation shaft 25-2 to transfer the pipette tip A toward the second region K2 (Step S65). In addition, when the presence of the pipette tip A is detected by the fourth detector 34 (Yes in Step S66), that is, when the pipette tip A is transferred up to the position immediately before the second region K2, the rotation of the rotation shaft 25-2 is stopped and the transfer is stopped (Step S67). The process proceeds to Step S62 and the same process is performed.

As shown in FIG. 4, the transport supply section 40 transports a pipette tip, supplied to the holder 41 of the first position P1, to the second position P2 for mounting a tip by moving the holder 41. The second position P2 is a position at which a tip is actually mounted on the sample dispensing arm 5 (aspiration nozzle 5a) shown in FIG. 1.

According to the pipette tip supplying apparatus 13 of this embodiment, when the presence of a pipette tip assembly B in the pipette tip storing section 20 is detected, the pipette tip assembly B is discharged to the outside of the pipette tip storing section 20. Therefore, the pipette tip assembly B is suppressed from being transported to the pipette tip mounting position from the pipette tip storing section, and thus pipette tips can be more securely supplied to the pipette tip mounting position one by one. For example, as shown in FIG. 5, it is possible to suppress the pipette tip assembly B from interfering with a single pipette tip A which is officially put on the first lifting member 26 and inhibiting the supply of the pipette tip A. Therefore, pipette tips A can be smoothly supplied to the tip mounting position one by one. In the sample analyzer 1 provided with the pipette tip supplying apparatus 13, since it is possible to suppress the generation of delay in the supply of pipette tips A, the sample dispensing by the sample dispensing arm 5 and the sample analysis by the analysis section 14 can be efficiently performed.

In the above-described embodiments, the widths of the pipette tip storing section 20, the first lifting member 26 and the like are smaller than the length L2 of a pipette tip assembly B in the longitudinal direction, and the first lifting member 26 is provided in the pipette tip storing section 20. A pipette tip A can be put on the upper surface 38 of the first lifting member 26 so that the longitudinal direction thereof is in the width direction of the pipette tip storing section 20, but a pipette tip assembly B cannot be put so that the longitudinal direction thereof is in the width direction of the pipette tip storing section 20. Therefore, the pipette tip assembly B cannot be put on the first lifting member 26 along the width direction of the pipette tip storing section 20, and as shown in FIG. 6, a part of the pipette tip assembly B is raised by the first lifting member 26 and is inclined and erected in the pipette tip storing section 20. In this state, the first detector 22 can detect the pipette tip assembly B. Therefore, the first detector 22 can detect the presence of the pipette tip assembly B by using the operation of the first lifting member 26.

The pipette tip supplying apparatus 13 and the sample analyzer 1 of the invention are not limited to the forms shown in the drawing, and may have other forms, respectively, in the scope of the invention.

For example, a camera which takes an image of the inside of the pipette tip storing section 20 may be provided in an upper section of the pipette tip storing section 20 to detect a pipette tip assembly B by image analysis. Otherwise, the first detector 22 may be a contact sensor which is disposed at a position which does not come into contact with a single pipette tip A, but comes into contact only with a pipette tip assembly B. In addition, a pipette tip in the pipette tip storing section 20 may be raised and the weight of the pipette tip may be measured to detect a pipette tip assembly B by using a difference in weight between the single pipette tip A and the pipette tip assembly B.

In addition, in the above-described embodiments, a pipette tip assembly B is erected by the first lifting member 26 to detect the pipette tip assembly B by the detector 22. However, the pipette tip assembly B may be erected by another mechanism. For example, a pipette tip assembly B may be raised by using an engaging member engaging with an opening at a proximal end of the pipette tip assembly.

In addition, in the above-described embodiments, a pipette tip is erected by the first lifting member 26 and a difference in length between a single pipette tip A and a pipette tip assembly B is used to detect only the pipette tip assembly. However, the invention is not limited thereto. For example, a moving mechanism may be provided which pushes out and moves a pipette tip in the pipette tip storing section 20 to the rear wall 18c from the first lifting member 26 by a predetermined distance and a detector may be disposed at a predetermined position (position at which when a pipette tip moving by the moving mechanism is a pipette tip assembly B, the pipette tip assembly B can be detected) on the side of the rear wall 18c to detect only a pipette tip assembly by using a difference in length between a single pipette tip A and a pipette tip assembly B.

In addition, by the first and second lifting members 26 and 27, a pipette tip A is raised from the pipette tip storing section 20 and supplied to the outside. However, the pipette tip A may be carried out by a belt conveyor or the like.

In addition, as illustrated by FIG. 11, the operation of discharging a pipette tip assembly is performed when a pipette tip assembly B is detected continuously a plural number of times. However, the discharging operation may be performed at the time when the pipette tip assembly B is detected first time. In addition, when the detection is set to be performed a plural number of times, the frequency of detection may not be three times.

In addition, in the above-described embodiments, when a pipette tip A is put on the first lifting member 26, the operation of discharging a pipette tip assembly B is not directly performed (No in Step S27 in FIG. 11). However, even when a pipette tip A is put on the first lifting member 26, the operation of discharging a pipette tip assembly B may be performed.

In addition, the pipette tip discharging section 23 may be provided to constitute at least a part of the bottom section of the pipette tip storing section 20 and to be able to open at least a part of the bottom section downward. Although not shown in the drawing, the pipette tip discharging section 23 may constitute the entire bottom section.

In addition, the pipette tip discharging section may have another configuration. For example, a pushing mechanism may be provided which is able to open the side wall of the pipette tip storing section 20 and pushes out a pipette tip assembly B in the pipette tip storing section 20 to the outside of the pipette tip storing section 20 from the opened part of the side wall. In addition, a catcher member may be provided which catches and can discharge a pipette tip assembly B in the pipette tip storing section 20 to the outside of the pipette tip storing section 20.

In addition, the above-described embodiments show an example of the application of the invention to the pipette tip supplying apparatus provided in an immunological analyzer which measures an antigen or an antibody in a sample. However, the invention may be applied to a sample analyzer using a pipette tip and may also be applied to, for example, a genetic amplification detecting device.

What is claimed is:

1. A pipette tip supplying apparatus configured to supply pipette tips that can include pipette tip assemblies in which a first pipette tip and a second pipette tip are coupled together with a distal end of the first pipette tip inserted into the second pipette tip, the apparatus comprising:
   a storing section that stores the pipette tips;
   a supplying section configured to supply at least one of the plurality of pipette tips stored in the storing section outside the storing section;
   a primary detector located at a predetermined distance from a bottom of the storing section so as to discriminate between a length of a pipette tip and a length of a pipette tip assembly,
   wherein the supplying section comprises a lifting member for lifting a pipette tip and a pipette tip assembly in the storing section, and
   the primary detector is disposed at a position at which the pipette tip assembly can be detected when the lifting member lifts the pipette tip assembly;

a discharging section configured to discharge the pipette tip assembly from the storing section; and a programmed controller coupled to the primary detector to receive detection signals therefrom and electrically connected to activate the supplying section and the discharging section, the controller programmed to determine when a pipette tip assembly is detected by the primary detector and to activate the discharge section.

2. The pipette tip supplying apparatus of claim 1,
wherein the length of the pipette tip assembly is greater than the length of anyone of the plurality of pipette tips and the storing section and the supplying section are dimensioned such that the pipette tip assembly is supplied in an upright orientation, and the primary detector detects the pipette tip assembly based on the difference in length between a single pipette tip and a pipette tip assembly.

3. The pipette tip supplying apparatus of claim 1, wherein the storing section has a length in a width direction which is larger than a length of a single pipette tip in a longitudinal direction and is smaller than a length of the pipette tip assembly in the longitudinal direction.

4. The pipette tip supplying apparatus of claim 3, wherein the lifting member is configured to lift a single pipette tip stored in the storing section with the longitudinal direction of the single pipette tip oriented in the width direction of the tip storing section, and the primary detector detects the pipette tip assembly when the pipette tip assembly is erected with one end of the pipette tip assembly lifted and the other end of the pipette tip assembly supported on a bottom of the tip storing section by a lifting operation of the lifting member.

5. The pipette tip supplying apparatus of claim 4, wherein the storing section is configured so that a pipette tip stored in the storing section moves toward the lifting member, and the primary detector is disposed on an upstream side of the lifting member in a direction in which the pipette tip in the storing section moves.

6. The pipette tip supplying apparatus of claim 5, wherein the bottom of the storing section is inclined relative to the lifting member.

7. The pipette tip supplying apparatus of claim 4, wherein the primary detector is disposed on a wall of the storing section at a position relative to the lifting member that is at a greater distance from the lifting member than the length of a single pipette tip erected in the storing section and is at a smaller distance from the lifting member than the length of the pipette tip assembly erected in the storing section.

8. The pipette tip supplying apparatus of claim 4, further comprising a second detector which detects a single pipette tip laid on the lifting member,
wherein the discharging section discharges the pipette tip assembly from the storing section when the pipette tip assembly in the storing section is detected by the primary detector and the single pipette tip is not detected by the second detector.

9. The pipette tip supplying apparatus of claim 1, wherein the discharging section discharges the pipette tip assembly from the storing section when the detector has detected the pipette tip assembly a plural number of times in a row with plural lifting operations of the lifting member.

10. The pipette tip supplying apparatus of claim 1, wherein the discharging section constitutes a part of a bottom of the storing section, and discharges the pipette tip assembly from the bottom of the storing section by opening the part of the bottom.

11. The pipette tip supplying apparatus of claim 10, wherein the discharging section comprises a plate-shaped member which constitutes the part of the bottom of the storing section and an actuator which rotates the plate-shaped member, and the discharging section discharges the pipette tip assembly from the bottom of the storing section by rotating the plate-shaped member by the actuator.

12. The pipette tip supplying apparatus of claim 10, further comprising a receiving section configured to receive the pipette tip assembly discharged by the discharging section at a position below the storing section.

13. The pipette tip supplying apparatus of claim 1, further comprising:
a tip input section which has a larger storage capacity for pipette tips than the storing section and into which a plurality of pipette tips are supplied by a user; and
a carry-in section configured to carry the pipette tips stored in the tip input section into the storing section.

14. A sample analyzer including a supplying section configured to supply pipette tips that can include pipette tip assemblies in which a first pipette tip and a second pipette tip are coupled together with a distal end of the first pipette tip inserted into the second pipette tip, the analyzer comprising:
a sample dispenser that comprises an aspiration nozzle on which a pipette tip is mounted and that is configured to dispense a sample with the pipette tip mounted on the aspiration nozzle;
an analysis section configured to analyze the sample dispensed by the sample dispenser;
a storing section that stores the pipette tips;
the supplying section configured to supply at least one of the plurality of the pipette tips stored in the storing section to a position at which a pipette tip is mounted on the aspiration nozzle;
a primary detector located at a predetermined distance from a bottom section of the supply section so as to discriminate between a length of a pipette tip and a length of a pipette tip assembly;
a discharging section configured to discharge the pipette tip assembly outside the tip storing section; and
a programmed controller coupled to the primary detector to receive detection signals therefrom and electrically connected to activate the sample dispenser and the supplying section, the controller programmed to determine when a pipette tip assembly is detected by the primary detector and to activate the discharging section.

\* \* \* \* \*